(12) United States Patent
Zhang et al.

(10) Patent No.: US 9,127,061 B2
(45) Date of Patent: Sep. 8, 2015

(54) ANTI-HUMAN P-CADHERIN (CDH3) RECOMBINANT ANTIBODY

(75) Inventors: Lilin Zhang, Tokyo (JP); Katsuyuki Mitomo, Tokyo (JP); Katsushi Kouda, Tokyo (JP); Yoko Kayukawa, Tokyo (JP)

(73) Assignee: PERSEUS PROTEOMICS INC., Tokyo (JP)

( * ) Notice: Subject to any disclaimer, the term of this patent is extended or adjusted under 35 U.S.C. 154(b) by 0 days.

(21) Appl. No.: 14/129,049

(22) PCT Filed: Jun. 19, 2012

(86) PCT No.: PCT/JP2012/065620
§ 371 (c)(1),
(2), (4) Date: Dec. 23, 2013

(87) PCT Pub. No.: WO2012/176765
PCT Pub. Date: Dec. 27, 2012

(65) Prior Publication Data
US 2014/0221620 A1    Aug. 7, 2014

(30) Foreign Application Priority Data

Jun. 24, 2011 (JP) ................. 2011-140407
Apr. 3, 2012 (JP) ................. 2012-084622

(51) Int. Cl.
| | |
|---|---|
| A61K 39/395 | (2006.01) |
| C07K 16/28 | (2006.01) |
| C07K 16/46 | (2006.01) |
| C12N 5/10 | (2006.01) |
| C12N 15/09 | (2006.01) |
| G01N 33/53 | (2006.01) |

(52) U.S. Cl.
CPC .............. *C07K 16/28* (2013.01); *A61K 39/395* (2013.01); *C07K 16/46* (2013.01); *C12N 5/10* (2013.01); *C12N 15/09* (2013.01); *G01N 33/53* (2013.01)

(58) Field of Classification Search
None
See application file for complete search history.

(56) References Cited

U.S. PATENT DOCUMENTS

| 8,455,249 B2 | 6/2013 | Aburatani et al. |
| 2013/0243771 A1 | 9/2013 | Aburatani et al. |
| 2013/0245232 A1* | 9/2013 | Aburatani et al. ......... 530/387.3 |

FOREIGN PATENT DOCUMENTS

| JP | 2005-522982 A | 8/2005 |
| JP | 2009-528257 A | 8/2009 |
| WO | WO 02/097395 A2 | 12/2002 |
| WO | WO 2007/102525 A1 | 9/2007 |
| WO | 2010/126137 | * 11/2010 |
| WO | WO 2010/126137 A1 | 11/2010 |

OTHER PUBLICATIONS

Brown et al (J. Immunol. May 1996; 156(9):3285-3291).*
Vajdos et al (J. Mol. Biol. Jul. 5, 2002;320(2); 415-428).*
Aaron C. Han et al.; Cadherin Expression in Glandular Tumors of the Cervix; Cancer; Nov. 15, 2000; vol. 89; No. 10; pp. 2053-2058.
Alan N. Houghton et al.; Mouse monoclonal IgG3 antibody detecting . . . ; Proc. Natl. Acad. Sci.; vol. 82; pp. 1242-1246; Feb. 1985.
Albert F. LoBuglio et al.; Mouse/human chimeric monoclonal antibody in man . . . ; Proc. Natl. Acad. Sci.; vol. 86, pp. 4220-4224; Jun. 1989.
Albert F. LoBuglio et al.; Phase I Trial of Multiple Large Doses of Murine . . . ; Journal of the National Cancer Institute; vol. 80; No. 12; Aug. 17, 1988; pp. 932-936.
Barbara M. Mueller et al.; Enhancement of Antibody-Dependent Cytotoxicity . . . ; The Journal of Immunology; vol. 144; No. 4; pp. 1382-1386; Feb. 15, 1990.
Chikako Yoshida et al.; Teratocarcinoma Cell Adhesion: Identification of a Cell-Surface Protein . . . ; Cell; vol. 28; pp. 217-224; Feb. 1982.
Daniel L. Shawler et al.; Human Immune Response to Multiple Injections . . . ; The Journal of Immunology; vol. 135; No. 2; pp. 1530-1535; Aug. 1985.
International Preliminary Report on Patentability dated Mar. 6, 2014 issued in PCT/JP2012/065620.
Joana Paredes et al.; P-cadherin expression in breast cancer . . . ; Breast Cancer Research; 2007; 9:214.
John Hakimi et al.; Reduced Immunogenicity and Improved Pharmacokinetics . . . ; The Journal of Immunology; vol. 147; No. 4; pp. 1352-1359; Aug. 15, 1991.
Katsunori Imai et al.; Identification of a Novel Tumor-Associated Antigen, Cadherin 3/P-Cadherin . . . ; Clin. Cancer Res.; 2008; 14(20); pp. 6487-6495; Oct. 15, 2008.
Keith O. Webber et al.; Preparation and Characterization of a Disulfide-Stabilized . . . ; Molecular Immunology; vol. 32; No. 4; pp. 249-258; 1995.
Lutz Riechmann et al.; Reshaping human antibodies for therapy; Nature; vol. 332; pp. 323-327; Mar. 24, 1988.

(Continued)

*Primary Examiner* — Sheela J Huff
(74) *Attorney, Agent, or Firm* — Birch, Stewart, Kolasch & Birch, LLP

(57) ABSTRACT

It is an object to provide a recombinant antibody that is an anti-CDH3 antibody having cytotoxicity on CDH3-expressing cells, which is anticipated to have fewer side effects than antibodies derived from animals other than humans and to maintain its therapeutic effects for a long period of time. The present invention provides a recombinant antibody which specifically reacts with an epitope existing in the amino acids at positions 108 to 131 or at positions 551 to 654 of the amino acid sequence shown in SEQ ID NO: 38 that is the extracellular region of human CDH3, and has cytotoxicity against CDH3-expressing cells.

9 Claims, 13 Drawing Sheets

(56) References Cited

OTHER PUBLICATIONS

M. B. Khazaeli et al.; Phase I Trial of Multiple Large Doses of Murine . . . ; J. Natl. Cancer Inst. vol. 80; No. 12; pp. 937-942; Aug. 17, 1988.

Malcolm V. Pimm et al.; The Characteristics of Blood-Borne Radiolabels . . . ; The Journal of Nuclear Medicine; 26; pp. 1011-1023; 1985.

Nigel S. Courtenay-Luck et al.; Development of Primary and Secondary Immune . . . ; Cancer Research; vol. 46; pp. 6489-6493; 1986.

Peter T. Jones et al.; Replacing the complementarity-determining regions in a human . . . ; Nature; vol. 321; pp. 522-525; May 1986.

Robert E. Bird et al.; Single-Chain Antigen-Binding Proteins; Science; 242; pp. 423-426; Oct. 21, 1988.

Robert O. Dillman et al.; Therapy of Chronic Lymphocytic Leukemia . . . ; Journal of Clinical Oncology; vol. 2; No. 8; pp. 881-891; Aug. 1984.

Sherie L. Morrison et al.; Chimeric human antibody molecules: Mouse antigen-binding . . . ; Proc. Natl. Acad. Sci.; vol. 81; pp. 6851-6855; Nov. 1984.

Takashi Yokota et al.; Rapid Tumor Penetration of a Single-Chain . . . ; Cancer Research; 52; pp. 3402-3408; 1992.

TC Meeker et al.; A clinical trial of anti-idiotype therapy for B cell malignancy; Blood; 65; 1985. pp. 1349-1363.

\* cited by examiner

Figure 1

```
E-cadherin_CDH1_    DWVIPPISCPENEKGPFPKNLVQIKSNKDKEGKVFYSITGQGADTPPVGVFIIERETGWL  60
P-cadherin_CDH3_    DWVVAPISVPENGKGPFPQRLNQLKSNKDRDTKIFYSITGPGADSPPEGVFAVEKETGWL  60
N-cadherin_CDH2_    DWVIPPINLPENSRGPFPQELVRIRSDRDKNLSLRYSVTGPGADQPPTGIFIINPISGQL  60

E-cadherin_CDH1_    KVTEPLDRERIATYTLFSHAVSSNGNAVEDPMEILITVTDQNDNKPEFTQEVFKGSVMEG 120
P-cadherin_CDH3_    LLNKPLDREEIAKYELFGHAVSENGASVEDPMNISIIVTDQNDHKPKFTQDTFRGSVLEG 120
N-cadherin_CDH2_    SVTKPLDREQIARFHLRAHAVDINGNQVENPIDIVINVIDMNDNRPEFLHQVWNGTVPEG 120

E-cadherin_CDH1_    ALPGTSVMEVTATDADDDVNTYNAAIAYTILSQDPELPDKNMFTINRNTGVISVVTTGLD 180
P-cadherin_CDH3_    VLPGTSVMQVTATDEDDAIYTYNGVVAYSIHSQEPKDPHDLMFTIHRSTGTIISVISSGLD 180
N-cadherin_CDH2_    SKPGTYVMTVTAIDADD-PNALNGMLRYRIVSQAPSTPSPNMFTINNETGDIITVAAGLD 179

E-cadherin_CDH1_    RESFPTYTLVVQAADLQGE---GLSTTATAVITVTDTNDNPPIFNPTTYKGQVPENEANV 237
P-cadherin_CDH3_    REKVPEYTLTIQATDMDGD---GSTTTAVAVVEILDANDNAPMFDPQKYEAHVPENAVGH 237
N-cadherin_CDH2_    REKVQQYTLIIQATDMEGNPTYGLSNTATAVITVTDVNDNPPEFTAMTFYGEVPENRVDI 239

E-cadherin_CDH1_    VITTLKVTDADAPNTPAWEAVYTILN-DDGGQFVVTTNPVNNDGILKTAKGLDFEAKQQY 296
P-cadherin_CDH3_    EVQRLTVTDLDAPNSPAWRATYLIMGGDDGDHFTITTHPESNQGILTTRKGLDFEAKNQH 297
N-cadherin_CDH2_    IVANLTVTDKDQPHTPAWNAVYRISGGDPTGRFAIQTDPNSNDGLVTVVKPIDFETNRMF 299

E-cadherin_CDH1_    ILHVAVTNVVPFEVSLTT---STATVTVDVLDVNEAPIFVPPEKRVEVSEDFGVGQEITS 353
P-cadherin_CDH3_    TLYVEVTNEAPFVLKLPT---STATIVVHVEDVNEAPVFVPPSKVVEVQEGIPTGEPVCV 354
N-cadherin_CDH2_    VLTVAAENQVPLAKGIQHPPQSTATVSVTVIDVNENPYFAPNPKIIRQEEGLHAGTMLTT 359

E-cadherin_CDH1_    YTAGEPDTFMEQKITYRIWRDTANWLEINPDTGAISTRAELDREDFEHVKNSTYTALIIA 413
P-cadherin_CDH3_    YTAEDPDK-ENQKISYRILRDPAGWLAMDPDSGQVTAVGTLDREDEQFVRNNIYEVMVLA 413
N-cadherin_CDH2_    FTAQDPDRYMQQNIRYTKLSDPANWLKIDPVNGQITTIAVLDRES-PNVKNNIYNATFLA 418

E-cadherin_CDH1_    TDNGSPVATGTGTLLLILSDVNDNAPIPEPRTIFFCER-NPKPQVINIIDADLPPNTSPF 472
P-cadherin_CDH3_    MDNGSPPTTGTGTLLLTLIDVNDHGPVPEPRQITICNQ-SPVRQVLNITDKDLSPHTSPF 472
N-cadherin_CDH2_    SDNGIPPMSGTGTLQIYLLDINDNAPQVLPQEAETCETPDPNSINITALDYDIDPNAGPF 478

E-cadherin_CDH1_    TAELTHG-ASANWTIQYNDPTQESIILKPK-MALEVGDYKINLKLMDNQN--KDQVTTLE 528
P-cadherin_CDH3_    QAQLTDD-SDIYWTAEVNE-EGDTVVLSLK-KFLKQDTYDVHLSLSDHGN--KEQLTVIR 527
N-cadherin_CDH2_    AFDLPLSPVTIKRNWTITRLNGDFAQLNLKIKFLEAGIYEVPIIITDSGNPPKSNISILR 538

E-cadherin_CDH1_    VSVCDCEGAAGVCRKAQPVEAGLQIPAILGILGGILALLILILLLLLFLRRR---AVVKE 585
P-cadherin_CDH3_    ATVCDCHGHVETC--PGPWKGGFILP----VLGAVLALLFLLLVLLLLVRKK---RKIKE 578
N-cadherin_CDH2_    VKVQQCDSNGDCTDVDRIVGAGLGTGAIIAILLCIIILLILVLMFVVWMKRRDKERQAKQ 598

E-cadherin_CDH1_    PLLPPEDDTRDNVYYYDEEGGGEEDQDFDLSQLHRG----LDARPEVT-RNDVAPTLMSV 640
P-cadherin_CDH3_    PLLLPEDDTRDNVFYYGEEGGGEEDQDYDITGLHRG----LEARPEVVLRNDVAPTIIPT 634
N-cadherin_CDH2_    LLIDPEDDVRDNILKYDEEGGGEEDQDYDLSQLQQPDTVEPDAIKPVGIRRMDERPIHAE 658

E-cadherin_CDH1_    PRYLPRPANPD--EIGNFIDENLKAADTDPTAPPYDSLLVFDYEGSGSEAASLSSLNSSE 698
P-cadherin_CDH3_    PMYRPRPANPD--EIGNFIIENLKAANTDPTAPPYDTLLVFDYEGSGSDAASLSSLTSSA 692
N-cadherin_CDH2_    PQYPVRSAAPHPGDIGDFINEGLKAADNDPTAPPYDSLLVFDYEGSGSTAGSLSSLNSSS 718

E-cadherin_CDH1_    SDKDQDYDYLNEWGNRFKKLADMYGGGEDD 728
P-cadherin_CDH3_    SDQDQDYDYLNEWGSRFKKLADMYGGGEDD 722
N-cadherin_CDH2_    SGGEQDYDYLNDWGPRFKKLADMYGGGDD- 747
```

CHO    CDH3 forced expression CHO

A B C

Figure 11
A
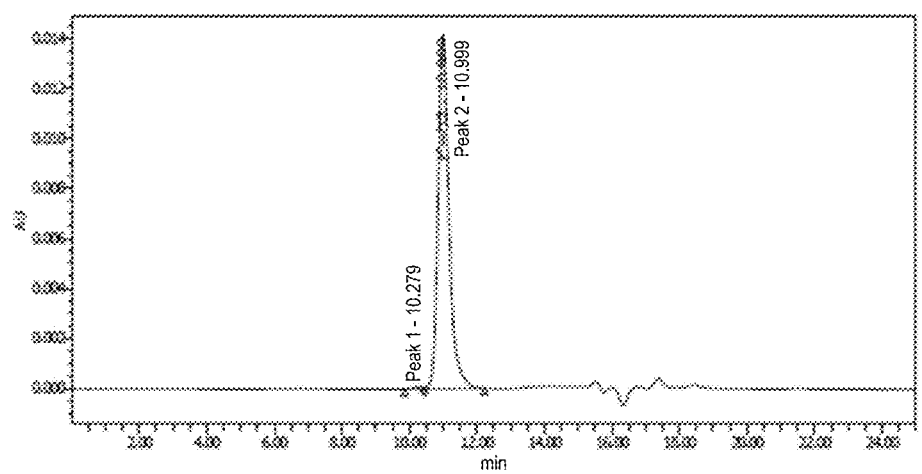
| | Component name | Retention time (min) | Area (μV sec) | % area | Height (μV) |
|---|---|---|---|---|---|
| 1 | Peak 1 | 10.279 | 1269 | 0.40 | 65 |
| 2 | Peak 2 | 10.999 | 314837 | 99.60 | 14171 |
B
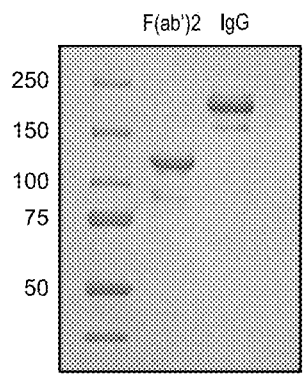

ANTI-HUMAN P-CADHERIN (CDH3) RECOMBINANT ANTIBODY

TECHNICAL FIELD

The present invention relates to a recombinant antibody that reacts with the extracellular region of human CDH3, recognizes a specific epitope, and has cytotoxicity.

BACKGROUND ART

Cancer is a serious disease that accounts for a major cause of death. However, therapeutic needs therefor have not yet been met. In recent years, in order to overcome the problem of conventional chemotherapy that causes damage even to normal cells, studies have been intensively conducted regarding cancer therapy using molecularly targeted agents, in which a drug targeting a specific molecule that is expressed specifically in a cancer cell is designed, and the therapy is then carried out using the drug.

CDH3 is a molecule in cancer cells that can be a target of molecular therapeutic agents (Non Patent Documents 1 and 2). CDH3 is a membrane protein that has been discovered as a molecule that is calcium-dependently associated with hemophilic cell adhesion (Non Patent Document 3). A protein, which has cadherin repeats (ECs) consisting of approximately 110 amino acid residues having high homology to one another, is referred to as a "cadherin superfamily." There are 120 or more types of such proteins, and they play an important role in the maintenance of multicellular organization. CDH3 is a member belonging to such a cadherin superfamily.

It has been reported that the expression of CDH3 in cancer tissues is higher than that in normal tissues (Non Patent Documents 1, 2, and 4). In cancer therapy, it has been studied to use a drug formed by binding an anticancer agent to an anti-human CDH3 antibody or an antibody having antibody-dependent cellular cytotoxicity (ADCC) for cancer cells in which the expression level of CDH3 is high (Patent Documents 1 to 3).

In recent years, many antibody drugs for cancer therapy have been actually on the market as molecular targeted drugs, and these drugs have provided therapeutic effects. The principal modes of action of these drugs include inhibition of signals associated with cell survival or cell growth and antibody-dependent cellular cytotoxicity (ADCC).

It has been generally known that when an antibody derived from an animal other than a human, such as a mouse antibody, is administered to a human, the administered antibody is recognized as a foreign substance, so that a human antibody against the mouse antibody (Human Anti Mouse Antibody: hereinafter referred to as "HAMA") is induced in the human body. It has been known that the HAMA reacts with the administered mouse antibody, and causes side effects (Non Patent Documents 5 to 8) or accelerates the disappearance of the administered mouse antibody from the body (Non Patent Documents 6, 9 and 10), thereby reducing the therapeutic effects of the mouse antibody (Non Patent Documents 11 and 12).

In order to overcome these problems, an attempt has been made to produce humanized antibodies, such as humanized chimeric antibodies or humanized complementarity determining region (hereinafter referred to as CDR)-grafted antibodies, from antibodies of animals other than humans by utilizing gene recombination technology. The humanized chimeric antibody means an antibody, in which the variable region (hereinafter referred to as a "V region") is the antibody of an animal other than a human and the constant region (hereinafter referred to as a "C region") is a human antibody (Non Patent Document 13). The humanized CDR-grafted antibody means an antibody, in which the amino acid sequence of CDR in the V region of the antibody of an animal other than a human is grafted into a suitable position of a human antibody (Non Patent Document 14). When compared with antibodies derived from animals other than humans, such as a mouse antibody, such humanized antibodies have various advantages for clinical application to humans. For example, with regard to immunogenicity and stability in blood, it has been reported that, upon administration of a humanized chimeric antibody to a human, the half-life in blood of the humanized chimeric antibody had been longer than that of a mouse antibody by approximately 6 times (Non Patent Document 15). In an experiment using monkeys, it has been reported that the immunogenicity of a humanized CDR-grafted antibody had been lower than that of a mouse antibody, and that the half-life in blood of the humanized CDR-grafted antibody had been longer than that of the mouse antibody by approximately 4 to 5 times (Non Patent Document 16). That is to say, a humanized antibody is anticipated to have fewer side effects than antibodies derived from animals other than humans and to maintain its therapeutic effects for a long period of time. In addition, cytotoxicity mediated by an Fc region of an antibody (a region that follows a hinge region on the heavy chain of an antibody), such as complement-dependent cytotoxicity (hereinafter referred to as "CDC activity") or antibody-dependent cellular cytotoxicity (hereinafter referred to as "ADCC activity"), is important to achieve therapeutic effects. Since the Fc region of a human antibody has a higher affinity for a human complement component or for an Fc receptor present on the surface of a human immune system effector cell as compared with the Fc region of a mouse antibody, it can be anticipated to provide more therapeutic effects. For instance, an increase in tumor cytotoxicity by human effector cells has been reported with regard to a humanized chimeric antibody in which the Fc region of a mouse antibody against GD2 is replaced with the Fc region of a human antibody (Non Patent Document 17). In addition, the same results as described above have been reported regarding a humanized CDR-grafted antibody against a CAMPATH-1 antigen (Non Patent Document 18). The aforementioned results demonstrate that a recombinant antibody is more preferable as an antibody for use in clinical application to humans, than an antibody derived from an animal other than a human.

Further, as a result of recent advances in the protein engineering and the genetic engineering, it has become possible to produce antibody fragments each having a small molecular weight, such as Fab, Fab', $F(ab)_2$, a single-chain antibody (hereinafter referred to as an "scFv") (Non Patent Document 19), and a disulfide-stabilized V region fragment (hereinafter referred to as a "dsFV") (Non Patent Document 20). Since these fragments have a molecular weight smaller than that of a complete antibody molecule, they are excellent in terms of transitivity to target tissues (Non Patent Document 21). Regarding these antibody fragments as well, a fragment derived from a recombinant antibody is more preferable as an antibody for use in clinical application to humans.

PRIOR ART DOCUMENTS

Patent Documents

Patent Document 1: WO2002/097395
Patent Document 2: WO2007/102525
Patent Document 3: WO2010/126137

Non Patent Documents

Non Patent Document 1: Clin Cancer Res., 14(20), 6487 (2008)
Non Patent Document 2: Breast Cancer Res., 9, 214 (2007)
Non Patent Document 3: Yoshida and Takeichi, Cell 28: 217-224, 1982
Non Patent Document 4: Cancer, 89(10), 2053 (2000)
Non Patent Document 5: J. Clin. Oncol., 2, 881 (1984)
Non Patent Document 6: Blood, 65, 1349 (1985)
Non Patent Document 7: J. Natl. Cancer Inst., 80, 932 (1988)
Non Patent Document 8: Proc. Natl. Acad. Sci., U.S.A., 82, 1242 (1985)
Non Patent Document 9: J. Nucl. Med., 26, 1011 (1985)
Non Patent Document 10: J. Natl. Cancer Inst., 80, 937 (1988)
Non Patent Document 11: J. Immunol., 135, 1530 (1985)
Non Patent Document 12: Cancer Res., 46, 6489 (1986)
Non Patent Document 13: Proc. Natl. Acad. Sci., U.S.A., 81, 6851 (1984)
Non Patent Document 14: Nature, 321, 522 (1986)
Non Patent Document 15: Proc. Natl. Acad. Sci., U.S.A., 86, 4220 (1989)
Non Patent Document 16: J. Immunol., 147, 1352 (1991)
Non Patent Document 17: J. Immunol., 144, 1382 (1990)
Non Patent Document 18: Nature, 332, 323 (1988)
Non Patent Document 19: Science, 242, 423 (1988)
Non Patent Document 20: Molecular Immunol., 32, 249 (1995)
Non Patent Document 21: Cancer Res., 52, 3402 (1992)

SUMMARY OF INVENTION

Problem to be Solved by the Invention

It is an object of the present invention to provide a recombinant antibody that is an anti-CDH3 antibody having cytotoxicity on CDH3-expressing cells, which is anticipated to have fewer side effects than antibodies derived from animals other than humans and to maintain its therapeutic effects for a long period of time.

Means for Solving the Object

The present inventors have obtained antibody H chain V region cDNA and L chain V region cDNA from hybridomas which produce mouse monoclonal antibodies against CDH3, namely, PPAT-057-06, PPAT-057-17, PPAT-057-13, PPAT-057-23, PPAT-057-27 and PPAT-057-12, and they have found that CDRs in the V regions have novel amino acid sequences. That is, cDNA encoding the H chain V region and the L chain V region each having such novel CDR were ligated to cDNA encoding a human antibody H chain C region and a human antibody L chain C region, respectively. The thus ligated genes were each incorporated into an animal cell expression vector to construct a chimeric antibody expression vector. The constructed expression vector was introduced into an animal cell, so that an anti-CDH3 chimeric antibody was allowed to express therein. The obtained anti-CDH3 chimeric antibody was then purified. The thus obtained antibody specifically reacted with human CDH3 and exhibited antibody-dependent cellular cytotoxicity (ADCC) on an antigen-positive cell line, and it had a tumor-suppressing effect on cancer-bearing mice. As described above, the present inventors have demonstrated the usefulness of the present antibody in living human bodies, and thus, the inventors have completed the present invention.

The present invention provides a recombinant antibody which specifically reacts with an epitope existing in the amino acids at positions 108 to 131 or at positions 551 to 654 of the amino acid sequence shown in SEQ ID NO: 38 that is the extracellular region of human CDH3, and has cytotoxicity against CDH3-expressing cells.

Preferably, the cytotoxicity is cell growth-suppressing activity or antibody-dependent cellular cytotoxicity (ADCC).

Preferably, the recombinant antibody is a humanized chimeric antibody, a humanized CDR-grafted antibody, or a human antibody.

Preferably, the recombinant antibody of the present invention comprises any of the amino acid sequences shown in SEQ ID NOS: 1-3, 7-9, 13-15, 19-21, 25-27 and 31-33, as each of the complementarity determining regions CDR1, CDR2 and CDR3 of the heavy chain variable region (HV) of the antibody, and/or which comprises any of the amino acid sequences shown in SEQ ID NOS: 4-6, 10-12, 16-18, 22-24, 28-30 and 34-36, as each of the complementarity determining regions CDR1, CDR2 and CDR3 of the light chain variable region (LV) thereof.

Preferably, the antibody of the present invention is a recombinant antibody which is selected from the following (1) to (6):
(1) a recombinant antibody, which comprises the CDR1, CDR2 and CDR3 of a heavy chain variable region (HV), respectively, consisting of the amino acid sequences shown in SEQ ID NOS: 1-3, and the CDR1, CDR2 and CDR3 of a light chain variable region (LV), respectively, consisting of the amino acid sequences shown in SEQ ID NOS: 4-6;
(2) a recombinant antibody, which comprises the CDR1, CDR2 and CDR3 of a heavy chain variable region (HV), respectively, consisting of the amino acid sequences shown in SEQ ID NOS: 7-9, and the CDR1, CDR2 and CDR3 of a light chain variable region (LV), respectively, consisting of the amino acid sequences shown in SEQ ID NOS: 10-12;
(3) a recombinant antibody, which comprises the CDR1, CDR2 and CDR3 of a heavy chain variable region (HV), respectively, consisting of the amino acid sequences shown in SEQ ID NOS: 13-15, and the CDR1, CDR2 and CDR3 of a light chain variable region (LV), respectively, consisting of the amino acid sequences shown in SEQ ID NOS: 16-18;
(4) a recombinant antibody, which comprises the CDR1, CDR2 and CDR3 of a heavy chain variable region (HV), respectively, consisting of the amino acid sequences shown in SEQ ID NOS: 19-21, and the CDR1, CDR2 and CDR3 of a light chain variable region (LV), respectively, consisting of the amino acid sequences shown in SEQ ID NOS: 22-24;
(5) a recombinant antibody, which comprises the CDR1, CDR2 and CDR3 of a heavy chain variable region (HV), respectively, consisting of the amino acid sequences shown in SEQ ID NOS: 25-27, and the CDR1, CDR2 and CDR3 of a light chain variable region (LV), respectively, consisting of the amino acid sequences shown in SEQ ID NOS: 28-30; and
(6) a recombinant antibody, which comprises the CDR1, CDR2 and CDR3 of a heavy chain variable region (HV), respectively, consisting of the amino acid sequences shown in SEQ ID NOS: 31-33, and the CDR1, CDR2 and CDR3 of a light chain variable region (LV), respectively, consisting of the amino acid sequences shown in SEQ ID NOS: 34-36.

Preferably, the antibody of the present invention comprises a deletion, addition, substitution and/or insertion of one or several amino acids with respect to any one or more amino acid sequences shown in SEQ ID NOS: 1-3, 7-9, 13-15, 19-21, 25-27 and 31-33, and which has cytotoxicity against CDR3-expressing cells that is equivalent to that of the aforementioned recombinant antibody of the present invention.

Preferably, the antibody of the present invention comprises a deletion, addition, substitution and/or insertion of one or several amino acids with respect to any one or more amino acid sequences shown in SEQ ID NOS: 4-6, 10-12, 16-18, 22-24, 28-30 and 34-36, and which has cytotoxicity against CDH3-expressing cells that is equivalent to that of the aforementioned recombinant antibody of the present invention.

Preferably, the recombinant antibody of the present invention comprises the constant region of a human antibody.

Preferably, the constant region of the human antibody consists to the constant region of a human antibody IgG1 class.

Preferably, the recombinant antibody is an antibody fragment selected from the group consisting of Fab, Fab', F(ab')$_2$, a single-chain antibody (scFv), a dimerized V region (Diabody), a disulfide-stabilized V region (dsFv) and a peptide comprising CDR.

The present invention provides DNA encoding the aforementioned recombinant antibody of the present invention.

The present invention provides a recombinant vector comprising the aforementioned DNA of the present invention.

The present invention provides a transformant obtained by introducing the aforementioned recombinant vector of the present invention.

The present invention provides a method for producing the recombinant antibody of the present invention, which comprises culturing the aforementioned transformant of the present invention. in a medium, generating and accumulating the recombinant antibody of the present invention in the culture, and then collecting the recombinant antibody from the culture.

The present invention provides a cytotoxic agent comprising the aforementioned recombinant antibody of the present invention as an active ingredient.

The present invention provides a therapeutic agent for high human CDH3 expression-related disease, which comprises the aforementioned recombinant antibody of the present invention as an active ingredient.

Preferably, the high CDH3 expression-related disease is cancer.

The present invention provides a diagnostic agent for high human CDH3 expression-related disease, which comprises the aforementioned recombinant antibody of the present invention as an active ingredient.

Preferably, the high CDH3 expression-related disease is cancer.

Advantageous Effects of Invention

The anti-CDH3 antibody of the present invention is characterized in that it is a recombinant antibody that recognizes the extracellular region of human CDH3 and has cytotoxicity. By utilizing genetic recombination technology, an antibody having low immunogenicity to humans and having cytotoxicity can be produced. The recombinant antibody of the present invention is anticipated to have fewer side effects than antibodies derived from animals other than humans and to maintain its therapeutic effects for a long period of time. The anti-human CDH3 recombinant antibody of the present invention can exhibit anticancer action by being administered to a cancer, in which CDH3 is expressed. That is to say, the anti-human CDH3 recombinant antibody of the present invention is useful as an anticancer agent.

BRIEF DESCRIPTION OF DRAWINGS

FIG. 1 shows the sequence of a mature protein of CDH3, from which the signal and propeptide sequences were removed (SEQ ID NOS: 96-98).

EMBODIMENT FOR CARRYING OUT THE INVENTION

Figure 2:
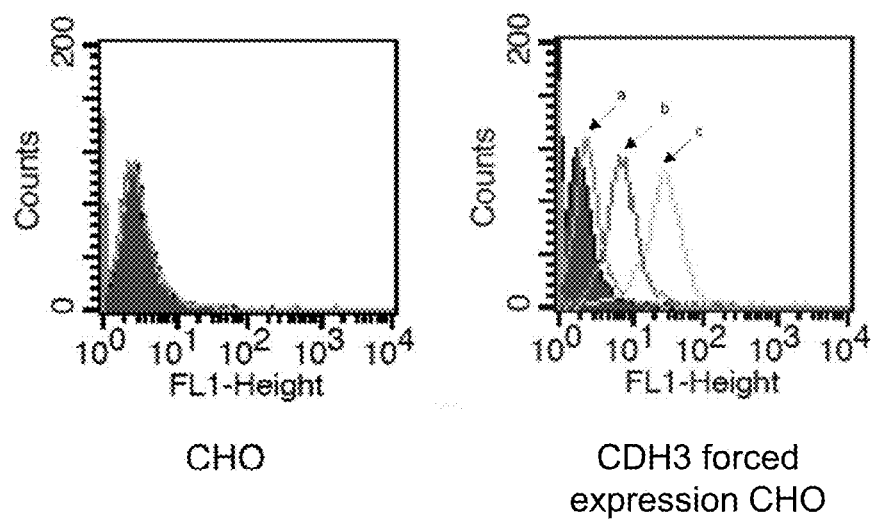
FIG. 2 shows the results of flow cytometry, in which a human CDH3 forced expression cell line was reacted with a commercially available anti-human CDH3 antibody. a: 0.01 µg/ml anti-CDH3 antibody, b: 0.1 µg/ml anti-CDH3 antibody, and c: 1 µg/ml anti-CDH3 antibody.

Hereinafter, the present invention will be described more in detail.

The antibody of the present invention is a recombinant antibody that recognizes the extracellular region of CDH3 and has cytotoxicity on CDH3-expressing cells, or an antibody fragment thereof. In particular, the present antibody is an antibody that specifically reacts with the regions of positions 108 to 131 or positions 551 to 654 of the amino acid sequence shown in SEQ ID NO: 38.

The term "humanized chimeric antibody" is used to mean an antibody consisting of the H chain V region (hereinafter also referred to as "VH") and L chain V region (hereinafter also referred to as "VL") of an antibody derived from an animal other than a human, and the H chain C region (hereinafter also referred to as "CH") and L chain C region (hereinafter also referred to as "CL") of a human antibody. As such an animal other than a human, any animals can be used, as long as they can produce hybridomas. Examples of such an animal include a mouse, a rat, a hamster, and a rabbit.

cDNA encoding VH and VL was obtained from hybridomas that produce a monoclonal antibody specifically reacting with human CDH3. The humanized chimeric antibody of the present invention can be produced by connecting these genes with cDNA encoding human antibody CH and human antibody CL, respectively, then incorporating each of the connected genes into an animal cell expression vector, and then introducing the expression vector into animal cells to allow the genes to express therein. Moreover, the obtained cDNA encoding VH and VL are inserted into the animal cell expression vectors having cDNA encoding human antibody CH and human antibody CL, respectively, and the obtained expression vectors are then introduced into animal cells to allow the genes to express therein, thereby producing the humanized chimeric antibody of the present invention.

(Production of Monoclonal Antibody)

To produce a monoclonal antibody, first of all, cadherin, or a partial peptide thereof (which is preferably any one of the upstream region of EC1, a cadherin domain 4 (EC4), and a cadherin domain 5 (EC5)), is administered as an antigen to a mammal such as a rat, a mouse or a rabbit. The amount of an antigen per animal is 0.1 to 100 mg if an adjuvant is not used, and is 1 to 100 µg when an adjuvant is used. Examples of such an adjuvant used herein include a Freund's complete adjuvant (FCA), a Freund's incomplete adjuvant (FIA), and an aluminum hydroxide adjuvant. Immunization is mainly carried out by injecting an antigen into the vein, subcutis or abdominal cavity. In addition, the immunization interval is not particularly limited, and the immunization is carried out at intervals of several days to several weeks, preferably at intervals of 2 to 5 weeks, 1 to 10 times, and more preferably 2 to 5 times. Thereafter, one to sixty days, and preferably one to fourteen days after the final immunization, antibody-producing cells are collected. Examples of the antibody-producing cells include splenic cells, lymph node cells, and peripheral blood cells. Among these cells, splenic cells or local lymph node cells are preferable.

To obtain cell fusion hybridomas, cell fusion of antibody-producing cells with myeloma cells is carried out. As myeloma cells to be fused with antibody-producing cells, commercially available cells that have been established from animals such as mice can be used. As an established cell line used herein, a cell line, which has drug selectivity, cannot survive in a HAT selection medium (containing hypoxanthine, aminopterin and thymidine) in an unfused state, and can survive therein only in a state in which it is fused with antibody-producing cells, is preferable. Examples of the myeloma cells include mouse myeloma cell lines such as P3X63-Ag.8.U1 (P3U1) or NS-1.

Subsequently, the aforementioned myeloma cells are fused with antibody-producing cells. Upon cell fusion, antibody-producing cells ($1 \times 10^6$ to $1 \times 10^7$ cells/ml) are mixed with myeloma cells ($2 \times 10^5$ to $2 \times 10^6$ cells/ml) in an animal cell culture medium containing no serum, such as DMEM or a RPMI-1640 medium (wherein the cell ratio between the antibody-producing cells and the myeloma cells is preferably 5:1), and a fusion is then carried out in the presence of a cell fusion promoter. As a cell fusion promoter, polyethylene glycol with a mean molecular weight of 1000 to 6000 Daltons or the like can be used. In addition, antibody-producing cells may also be fused with myeloma cells using a commercially available cell fusion apparatus that utilizes electrical stimulation (e.g. electroporation).

After completion of the cell fusion treatment, hybridomas of interest are selected from the resulting cells. As a selection method, a cell suspension is appropriately diluted, for example, with a fetal bovine serum-containing RPMI-1640 medium, and the resulting cell suspension is inoculated at approximately $3 \times 10^5$ cells/well on a microtiter plate. Thereafter, a selection medium is added to each well, and a culture is then carried out, while exchanging the selection medium with a fresh one, as appropriate. As a result, cells growing approximately 14 days after initiation of the culture in the selection medium can be obtained as hybridomas.

Thereafter, the presence or absence of an antibody of interest in a culture supernatant of the growing hybridomas is screened. The screening of hybridomas may be carried out according to an ordinary method, and the type of the screening method is not particularly limited. For instance, an aliquot of the culture supernatant of the growing hybridomas contained in a well is collected, and it is then subjected to enzyme immunoassay, radioimmunoassay or the like, so that hybridomas that produce an antibody binding to the upstream region of EC1 of cadherin, the EC4 domain, or the EC5 domain can be screened. The fused cells are cloned according to limiting dilution or the like, and thus, hybridomas can be finally established as cells that produce a monoclonal antibody.

As a method of collecting a monoclonal antibody from the established hybridomas, an ordinary cell culture method, an ascites extraction method or the like can be adopted. In the cell culture method, hybridomas are cultured in an animal cell culture medium, such as a 10% fetal bovine serum-containing RPMI-1640 medium, an MEM medium or a serum-free medium, under common culture conditions (e.g. 37° C. and 5% $CO_2$) for 7 to 14 days, and thereafter, an antibody is obtained from the culture supernatant.

In the ascites extraction method, approximately $1 \times 10^7$ hybridomas are administered into the abdominal cavity of an animal of the same species as a mammal from which the myeloma cells have been derived, so as to allow large quantities of hybridomas to grow therein. Then, one or two weeks later, ascites is collected. When purification of an antibody is required in the aforementioned antibody collection methods, known methods, such as ammonium sulfate precipitation, ion exchange chromatography, gel filtration and affinity chromatography, are selected as appropriate, or these methods are used in combination, so as to purify the antibody.

(Humanized Chimeric Antibody)

The CH of a humanized chimeric antibody is not particularly limited, as long as it belongs to a human immunoglobulin (hereinafter referred to as "hIg"). Those of hIgG class are preferable, and any one of subclasses belonging to the hIgG class, such as hIgG1, hIgG2, hIgG3 or hIgG4, may be used. In addition, the CL of a humanized chimeric antibody is not particularly limited, as long as it belongs to Mg, and those of κ class or λ class can be used.

The term "humanized CDR-grafted antibody" is used to mean an antibody, in which the amino acid sequences of CDRs in the VH and VL of an antibody derived from an animal other than a human are transplanted into suitable positions in the VH and VL of a human antibody.

Such a humanized CDR-grafted antibody can be produced by: constructing cDNA encoding V regions, in which the amino acid sequences of CDRs in the VH and VL of an antibody that is derived from an animal other than a human and specifically reacts with human CDH3 have been transplanted into the FRs in the VH and VL of any given human antibody; then inserting the cDNA into animal cell expression vectors comprising DNA encoding the CH and CL of a human antibody, respectively, so as to construct humanized CDR-grafted antibody expression vectors; and then introducing the constructed expression vectors into animal cells, so that the genes are allowed to express therein.

Among host cell systems used for protein expression, many antibody-producing host cell systems are derived from mammals. The manufacturers may preferentially determine a specific host cell system most suitable for a gene product to be expressed. Examples of a common host cell system include, but are not limited to, a CHO-derived cell line (a Chinese hamster ovary cell line), CV1 (a monkey kidney system), COS (a derivative of CV1 to an SV40T antigen), SP2/0 (mouse myelomas), P3x63-Ag3.653 (mouse myelomas), 293 (human kidney), and 293T (a derivative of 293 to an SV40T antigen). Such a host cell system is available from commercial facilities or the American Tissue Culture Collection (ATCC), or also from institutions for publishing some publications.

Preferably, the host cell system is either a CHO-derived cell line comprising defective expression of a dgfr gene, or SP2/0. For such a CHO-derived cell line and SP2/0, see Urland, G et al., Effect of gamma rays at the dihydrofolate reductase locus: deletions and inversions, Somat. Cell. Mol. Genet. Vol. 12, 1986, pp. 5555-566, and Schulman, M. et al., A better cell line for making hybridomas secreting specific antibodies, Nature Vol. 276, 1978, pp. 269-270, respectively. Most preferably, the host cell system is DHFR-deficient CHO. Transfection of a plasmid into a host cell can be achieved by any given technique. Specific examples of such a transfection method include, but are not limited to, transfection (including a calcium phosphate method, a DEAE method, lipofection, and electroporation), a method of introducing DNA utilizing an envelope such as Sendai virus, microinjection, and infection using viral vectors such as retrovirus or adenovirus. For such transfection methods, see Current Protocols in Molecular Biology, Chapter 9 Introduction of DNA into Mammalian Cells, John Wiley and Sons, Inc. Introduction of a plasmid into a host by electroporation is most preferable.

A method of obtaining a human antibody has also been known. For example, human lymphocytes are sensitized with a desire antigen or a cell expressing such a desired antigen in vitro, and the sensitized lymphocytes are then fused with human myeloma cells, such as U266, so as to obtain a desired human antibody having an activity of binding to an antigen (see JP Patent Publication (Kokoku) No. 1-59878 B (1989)). Also, a desired human antibody can be obtained by immunizing a transgenic animal having all repertoires of human antibody genes with a desired antigen (see WO93/12227, WO92/03918, WO94/02602, WO94/25585, WO96/34096, and WO96/33735). Moreover, a technique of obtaining a human antibody by panning using a human antibody library has also been known. For example, the variable region of a human antibody is allowed to express on the surface of phages as a single-chain antibody (scFv) according to a phage display method, and a phage binding to an antigen can be then selected. By analyzing the selected phage gene, a DNA sequence encoding the variable region of a human antibody binding to the antigen can be determined. If the DNA sequence of the scFv binding to the antigen could be determined, it would be possible to produce a suitable expression vector using the determined sequence and to obtain a human antibody. These methods have already been well known, and WO92/01047, WO92/20791, WO93/06213, WO93/11236, WO93/19172, WO95/01438, and WO95/15388 can be referred to.

An antibody comprising a deletion, addition, substitution and/or insertion of one or several (preferably 1 to 10, more preferably 1 to 5, and further preferably 1 to 3) amino acids with respect to the aforementioned amino acid sequences and also specifically reacting with human CDH3 having the above-mentioned properties, or an antibody fragment thereof, is also included in the scope of the present invention.

According to a preferred aspect, the recombinant antibody of the present invention comprises any one of the amino acid sequences shown in SEQ ID NOS: 1-3, 7-9, 13-15, 19-21, 25-27 and 31-33, as each of the complementarity determining regions CDR1, CDR2 and CDR3 of the heavy chain variable region (HV) of the antibody, and/or any one of the amino acid sequences shown in SEQ ID NOS: 4-6, 10-12, 16-18, 22-24, 28-30 and 34-36, as each of the complementarity determining regions CDR1, CDR2 and CDR3 of the light chain variable region (LV) thereof.

A mutant of the recombinant antibody, which comprises a deletion, addition, substitution and/or insertion of one or several (preferably 1 to 5, more preferably 1 to 4, further preferably 1 to 3, and particularly preferably 1 or 2) amino acids with respect to the aforementioned amino acid sequences and which has cytotoxicity on CDH3-expressing cells that is equivalent to that of the above-described recombinant antibody of the present invention, is also included in the scope of the present invention. Furthermore, a mutant of the recombinant antibody, which has high identity to the aforementioned amino acid sequences and which has cytotoxicity on CDH3-expressing cells that is equivalent to that of the above-described recombinant antibody of the present invention, is also included in the scope of the present invention. It is to be noted that the term "high identity" is generally used in the present invention to mean that a certain antibody has an identity of 70% or more, preferably 80% or more, more preferably 90% or more, further preferably 95% or more, still further preferably 97% or more, still further preferably 99% or more, and particularly preferably 99.5% or more at the amino acid sequence level with another antibody. Such identity can be determined according to the algorithm described by Wilbur, W. J. and Lipman D. J. (Wilbur, W. J. and Lipman, D. J. Proc. Natl. Acad. Sci. U.S.A. (1983) 80, 726-730).

In addition, in the present invention, with regard to mutants of the recombinant antibody, which are specified to comprise a deletion, addition, substitution and/or insertion of amino acid(s) with respect to the above-mentioned amino acid sequences or are specified with identity (%), when the cytotoxicity of such mutants on CDH3-expressing cells is "equivalent" to that of the original recombinant antibody, from which the mutants are derived, it means that, when the cytotoxicity of the original recombinant antibody on any CDH3-expressing cells is defined as 100%, the mutant antibody has a cytotoxic activity of 60% or more, more specifically 70% or more, and further specifically 80% or more of the cytotoxicity of the original one, unless otherwise specified. Regarding the measurement of the cytotoxicity of an antibody on CDH3-expressing cells, several means have been known. If a mutant antibody can be confirmed to have the above-described cytotoxic activity by any one of the means, the cytotoxicity of the mutant antibody on CDH3-expressing cells can be considered to be "equivalent".

The phase "comprise a deletion, substitution, insertion or addition of one or more amino acid residues with respect to the amino acid sequence of the present invention" means that one or multiple amino acid residues are deleted, substituted, inserted or added in any given positions in a single amino acid sequence or in one or multiple amino acid sequences. A deletion, a substitution, an insertion, and an addition may take place simultaneously. The substituted, inserted or added amino acid residues may be either naturally occurring or non-naturally occurring amino acid residues.

(Antibody Fragments)

The recombinant antibody of the present invention may be an antibody fragment. Examples of such an antibody fragment include Fab, Fab', F(ab')$_2$, scFv, dsFv, and a peptide containing CDR.

Fab is an antibody fragment obtained by digesting IgG with a protease, papain (wherein the IgG is cut at the amino acid residue at position 224 on the H chain), in which about a half on the N-terminal side of the H chain is bound to the entire L chain via a disulfide bond, and the antibody fragment has a molecular weight of approximately 50,000 and has an antigen-binding activity The Fab of the present invention can be obtained by digesting an antibody specifically reacting with CDH3 with a protease, papain. Alternatively, DNA encoding the Fab of the antibody is inserted into a prokaryote expression vector or a eukaryote expression vector, and the obtained vector is then introduced into a prokaryote or a eukaryote to allow Fab to express therein, thereby producing Fab.

F(ab')$_2$ is an antibody fragment obtained by digesting IgG with a protease, pepsin (wherein the IgG is cut at the amino acid residue at position 234 on the H chain), wherein the antibody fragment is slightly larger than those obtained by binding Fab to another Fab via a disulfide bond in the hinge region thereof, has a molecular weight of approximately 100,000, and has an antigen-binding activity.

The F(ab')$_2$ of the present invention can be obtained by digesting an antibody specifically reacting with CDH3 with a protease, pepsin. Alternatively, the present F(ab')$_2$ can also be produced by binding the below-mentioned Fab' to another Fab' via a thioether bond or a disulfide bond.

Fab' is an antibody fragment obtained by cutting a disulfide bond in the hinge region of the aforementioned F(ab')$_2$, wherein the antibody fragment has a molecular weight of approximately 50,000 and has an antigen-binding activity.

The Fab' of the present invention can be obtained by treating F(ab')$_2$ specifically reacting with CDH3 with a reducing agent, dithiothreitol. Alternatively, DNA encoding a Fab' fragment of the antibody is inserted into a prokaryote expression vector or a eukaryote expression vector, and the obtained vector is then introduced into a prokaryote or a eukaryote to allow Fab' to express therein, thereby producing Fab'.

scFv means a VH-P-VL or VL-P-VH polypeptide formed by ligating a single VH to a single VL using a suitable peptide linker (hereinafter referred to as "P"). As VH and VL contained in the scFv of the present invention, those derived from the antibody of the present invention that specifically reacts with CDH3, namely, either humanized antibodies or human antibodies can be used.

The scFv of the present invention can be produced by obtaining cDNA encoding the VH and VL of an antibody specifically reacting with CDH3, constructing DNA encoding scFv, inserting the constructed DNA into a prokaryote expression vector or a eukaryote expression vector, and introducing the obtained expression vector into a prokaryote or a eukaryote, so as to allow scFv to express therein.

dsFv means a polypeptide, in which a single amino acid residue in each of VH and VL has been substituted with a cysteine residue and the resulting VH is then bound to the resulting VL via a disulfide bond between the cysteine residues. The amino acid residue to be substituted with the cysteine residue can be selected based on prediction of the antibody conformation according to the method of Reiter et al. (Protein Engineering, 7, 697 (1994)). As VH and VL contained in the dsFv of the present invention, those derived from the antibody of the present invention that specifically reacts with CDH3, namely, either humanized antibodies or human antibodies can be used.

The dsFv of the present invention can be produced by obtaining cDNA encoding the VH and VL of an antibody specifically reacting with CDH3, constructing DNA encoding dsFv, inserting the constructed DNA into a prokaryote expression vector or a eukaryote expression vector, and introducing the obtained expression vector into a prokaryote or a eukaryote, so as to allow dsFv to express therein.

(Peptide Comprising CDR)

A peptide comprising CDR is configured to comprise at least one region of H chain or L chain CDR. A plurality of CDRs can be bound directly or via a suitable peptide linker. The peptide comprising CDR of the present invention can be produced by obtaining cDNA encoding the VH and VL of an antibody specifically reacting with CDH3, constructing DNA encoding CDR, inserting the constructed DNA into a prokaryote expression vector or a eukaryote expression vector, and introducing the obtained expression vector into a prokaryote or a eukaryote, so as to allow a peptide comprising CDR to express therein.

Moreover, a peptide comprising CDR can also be produced by chemical synthesis methods such as an Fmoc method (fluorenylmethyloxycarbonyl method) or a tBoc method (t-butyloxycarbonyl method).

(Reactivity with CDH3-Expressing Cells)

To examine reactivity with CDH3-expressing cells, CDH3 expressed on the cell surface can be examined with a flow cytometer, for example.

The antibody used in flow cytometry may be either an antibody labeled with a fluorescent substance such as FITC or with biotin, or an unlabeled antibody. A fluorescently-labeled avidin, a fluorescently-labeled anti-human immunoglobulin antibody, or the like is used, depending on the presence or absence of labeling of the antibody used and the type thereof. Reactivity can be evaluated by adding a sufficient amount of anti-CDH3 antibody (generally having a final concentration of 0.1 to 10 μg/mL) to an analyte, and then by comparing the obtained reactivity with the reactivity with a negative control antibody or a positive control antibody.

(Cytotoxicity)

Cytotoxicity includes ADCC activity, CDC activity and cell growth inhibitory activity, which are exhibited either in vivo or in vitro.

Antibody-dependent cellular cytotoxicity (ADCC activity) and CDC can be measured by known methods (Cancer Immunol. Immunother., 36, 373 (1993)). For example, ADCC activity can be measured by allowing target cells expressing CDH3 serving as an antigen to come into contact with effector cells, such as peripheral blood monocytes, monocytes, macrophages or granulocytes, collected from a human or other animals in the presence of an antibody, then detecting the degree of damaged target cells, and then quantifying the detected degree of the damaged target cells. The degree of damaged target cells can be detected by a $^{51}$Cr release assay, a method of detecting the enzymatic activity of the target cells, a detection method using flow cytometer, etc. The effects of the medicament of the present invention in an ADCC activity measurement system, can be measured by adding a drug to the ADCC activity measurement system, or by exposing such a drug to target cells or effector cells, or to both of them for a certain period of time, and then observing the effects of the drug on ADCC activity.

The cell growth inhibitory activity may be either an activity of slowing the growth of cells in vitro or an activity of slowing the growth of tumor cells in vivo. For example, the cell growth inhibitory activity can be measured in vitro according to an ordinary cell growth measurement method (e.g. the method described in Blood, 104 (4) 1137 (2004); J Biol. Chem., 279 (4), 2856 (2004)). Examples of an in vivo animal model include: a xenograft model prepared by transplanting a human cancer tissue-derived cultured cell line into an immunodeficient mouse such as a nude mouse; and a syngeneic graft model prepared by transplanting a cultured mouse cancer cell line into a wild-type mouse having a normal immune system.

A xenograft model can be produced by transplanting a human cancer cell line into various sites of immunodeficient mice such as a nude mouse, including the subcutis, intradermal site, abdominal cavity, or vein.

(Cytotoxic Agent, and Therapeutic Agent and Diagnostic Agent for High Human CDH3 Expression-Related Disease)

Since the antibody of the present invention exhibits high cytotoxicity, it can be used as a cytotoxic agent. Moreover, the antibody of the present invention can be used as a therapeutic agent or a diagnostic agent for high human CDH3 expression-related disease. The cytotoxic agent and therapeutic agent for high human CDH3 expression-related disease of the present invention can cause damage to cancer cells, for example, by allowing the agents to come into contact with cancer cells expressing cadherin. Examples of the high human CDH3 expression-related disease include colon cancer, breast cancer, ovarian cancer, endometrial cancer, cervical cancer, lung cancer, transitional cell carcinoma, pancreatic cancer, hepatic cancer, kidney cancer, biliary tract cancer, thyroid cancer, head and neck cancer, esophageal cancer, cutaneous squamous cell cancer, melanoma, stomach cancer, prostate cancer, bladder cancer, osteosarcoma, and soft tissue sarcoma.

The cytotoxic agent, therapeutic agent, and diagnostic agent of the present invention may appropriately comprise pharmaceutically acceptable carriers, excipients, diluents, etc. as necessary, as well as the antibody of the present invention. The cytotoxic agent, therapeutic agent, and diagnostic agent of the present invention can be formulated in the form of an injection, for example. The administration amount of the cytotoxic agent, therapeutic agent, or diagnostic agent of the present invention depends on the degree of symptom, age and body weight of a patient, an administration method, etc. The weight of the antibody as an active ingredient is generally in the range from approximately 10 ng to approximately 100 mg/kg body weight.

The present invention will be more specifically described in the following examples. However, these examples are not intended to limit the scope of the present invention.

EXAMPLES

Example 1

Establishment of CHO Cell Line Expressing CDH3

In order to obtain a cell line used in screening for an anti-CDH3 antibody, CHO cells expressing the full-length CDH3 were established.
(1) Construction of CDH3 Gene Expression Vector In order to insert the full-length human CDH3 DNA shown in SEQ ID NO: 37 into a mammalian expression vector pEF4/myc-HisB (Invitrogen), the DNA was digested with two types of restriction enzymes, KpnI (TAKARA BIO INC.) and XbaI (TAKARA BIO INC.), at 37° C. for 1 hour. Thereafter, the resulting DNA was inserted into pEF4/myc-HisB that had also been digested with KpnI and XbaI according to an ordinary method using T4 DNA ligase (Promega), thereby obtaining an expression vector, pEF4-CDH3-myc-His.
(2) Obtainment of CDH3 Stable Expression Cell Line On the day before transfection, CHO cells ($8 \times 10^5$) were inoculated on a dish with a diameter of 10 cm in accordance with the protocols included with FuGENE (registered trademark) 6 Transfection Reagent (Roche Diagnostics), and they were then cultured overnight. Thereafter, 8 μg of the expression vector pEF4-CDH3-myc-His and 16 μL of the FuGENE 6 reagent were mixed into 400 μL of a serum-free RPMI1640 medium (SIGMA-ALDRICH), and the obtained mixture was then left at room temperature for 15 minutes. Thereafter, the reaction mixture was added to the cell culture, so as to perform transfection. Two days after the transfection, cloning was carried out by limiting dilution using a selective reagent (Zeocin (registered trademark)).

The selection of CDH3 full-length expression CHO clone were carried out by a Western blotting method using Anti-c-Myc Monoclonal Antibody (SANTA CRUZ BIOTECHNOLOGY). As a result, a CDH3 full-length expression CHO cell line (EXZ1501) having a high expression level and a high growth rate was obtained. The measurement results obtained by examining the reactivity of this cell line with a commercially available anti-CDH3 antibody (R & D SYSTEMS) by flow cytometry are shown in FIG. 2.

Example 2

Production of Soluble CDH3 Antigen

In order to be used as an immunogen in the production of an anti-CDH3 antibody, a soluble CDH3-(sCDH3) protein, in which its C-terminal transmembrane region and the subsequent regions were deleted, was produced.
(1) Construction of Soluble CDH3 Antigen Expression Vector Using full-length CDH3 cDNA as a template, a PCR reaction was carried out employing a forward primer (SEQ ID NO. 39: CGCGGTACCATGGGGCTCCCTCGT, (hCDH3 Full FW)) and a reverse primer (SEQ ID NO. 40: CCGTCTA-GATAACCTCCCTICCAGGGTCC, (hCDH3 Solb RV)) that had been designed to amplify a region corresponding to the CDH3 extracellular region (which corresponded to positions 1-654 of SEQ ID NO. 38). KOD-Plus (Toyobo Co., Ltd.) was used in the reaction, and the reaction was carried out under reaction conditions consisting of 30 cycles of 94° C.-15 seconds, 55° C.-30 seconds, and 68° C.-90 seconds.

Thereafter, a gel fragment containing an approximately 2.0-kbp band that was a size of interest was cut out in agarose gel electrophoresis, and using QIA (registered trademark) Quick Gel Extraction Kit (QIAGEN), sCDH3 cDNA of interest was obtained.

In order to insert this sCDH3 cDNA into an expression vector pEF4/myc-HisB, the DNA was digested with two types of restriction enzymes KpnI and XbaI, and it was then inserted into pEF4/myc-HisB that had also been digested with KpnI and XbaI according to an ordinary method using T4 DNA ligase, so as to obtain an expression vector pEF4-sCDH3-myc-His.
(2) Expression of Soluble CDH3 (sCDH3) Protein On the day before transfection, CHO cells ($8 \times 10^5$) were seeded on a dish with a diameter of 10 cm in accordance with the protocols included with the FuGENE 6 Transfection Reagent, and they were then cultured overnight. Thereafter, 8 µg of the expression vector pEF4-CDH3-myc-His and 16 µL of the FuGENE 6 reagent were mixed into 400 µL of a serum-free RPMI1640 medium, and the mixture was then left at room temperature for 15 minutes. Thereafter, the mixture was added to the cell culture, so as to perform transfection. Two days after the transfection, cloning was carried out by limiting dilution using a selective reagent (Zeocin).

Soluble CDH3-expressing CHO cells were selected according to a Western blot method using an anti-c-Myc monoclonal antibody (SANTA CRUZ BIOTECHNOLOGY). It was attempted to select a cell line, which was able to secrete a large amount of soluble CDH3 into the culture supernatant and which was able to grow favorably. As a result, a soluble CDH3-expressing CHO cell line (EXZ1702) was obtained. Using three roller bottles each having a culture area of 1,500 $cm^2$, the selected soluble CDH3-expressing CHO cell line (EXZ1702) was cultured for 72 hours in 333 mL of a serum-free medium CHO-S-SFM-II (Invitrogen) per roller bottle. Thereafter, a culture supernatant was recovered. A soluble CDH3 protein was obtained from the recovered culture supernatant according to affinity chromatography using HisTrap (registered trademark) HP column (GE Healthcare Biosciences) and gel filtration chromatography using Superdex (registered trademark) 200 pg column (GE Healthcare Biosciences).

Example 3

Generation of Anti-CDH3 Monoclonal Antibody (1) Production of Monoclonal Antibody Using Soluble CDH3 Protein as Immunogen 50 µg of a soluble CDH3 protein dissolved in a normal saline and Titer-MAX Gold (registered trademark) (Titer-Max) were mixed in equal volumes. The obtained mixture was injected into the abdominal cavity and subcutis of each MRL/lpr mouse (Japan SLC, Inc.), so as to carry out initial immunization. The second immunization and the subsequent immunizations were carried out by mixing a soluble CDH3 protein (protein amount: 25 µg) that had been prepared in the same manner as described above with Titer-MAX gold and then injecting the obtained mixture into the abdominal cavity and subcutis of the mouse. Three days after the final immunization, splenic cells were aseptically prepared from the mouse, and the splenic cells were then fused with mouse myeloma cells SP2/O-Ag14 or P3-X63-Ag8.653 according to an ordinary method (polyethylene glycol method).

(2) Selection of Anti-CDH3 Antibody-Producing Hybridomas

An anti-CDH3 antibody was selected by flow cytometry using a CHO cell line (EXZ1501) expressing full-length CDH3.

Specifically, the CHO cell line (EXZ1501) that expressed full-length CDH3 was treated with 2 mM EDTA-PBS, so that it was removed from the culture plate. Thereafter, the cells were suspended in a FACS solution at $1 \times 10^6$ cells/mL. This cell suspension was inoculated on a 96-well plate at 50 µL/well, and a culture supernatant of hybridomas was then added thereto, so that they were reacted at 4° C. for 60 minutes. Thereafter, the reaction solution was washed out with a FACS solution (200 µL/well) two times, and AlexaFluor 488-labeled anti-mouse IgG-goat F(ab')$_2$ (Invitrogen) was then added to the resultant. Then, the mixture was reacted at 4° C. for 30 minutes. Thereafter, the reaction solution was washed out with a FACS solution two times, and it was then subjected to flow cytometry, so as to select hybridomas that were strongly reacted with the CDH3-expressing CHO cells. Thus, hybridomas producing mouse antibodies PPAT-057-06, PPAT-057-17, PPAT-057-13, PPAT-057-23, PPAT-057-27, and PPAT-057-12 were obtained. The hybridoma cell producing the mouse antibody PPAT-057-17 (Accession No. NITE BP-865) was deposited under the terms of the Budapest Treaty with the International Patent Organism Depositary, the National Institute of Technology and Evaluation, an Independent Administrative Institution under the Ministry of Economy, Trade and Industry (2-5-8, Kazusa Kamatari, Kisarazu-shi, Chiba-ken, Japan, postal code: 292-0818) on Jan. 20, 2010. It is to be noted that hybridomas producing the mouse antibody PPAT-057-12 described in Japanese Patent Application No. 2011-140407 are the same as the hybridoma cells producing the mouse antibody PPAT-057-17 in the present application. That is to say, the mouse antibody PPAT-057-12 described in Japanese Patent Application No. 2011-140407 was renumbered to as a "mouse antibody PPAT-057-17" in the present application.

Figure 3:
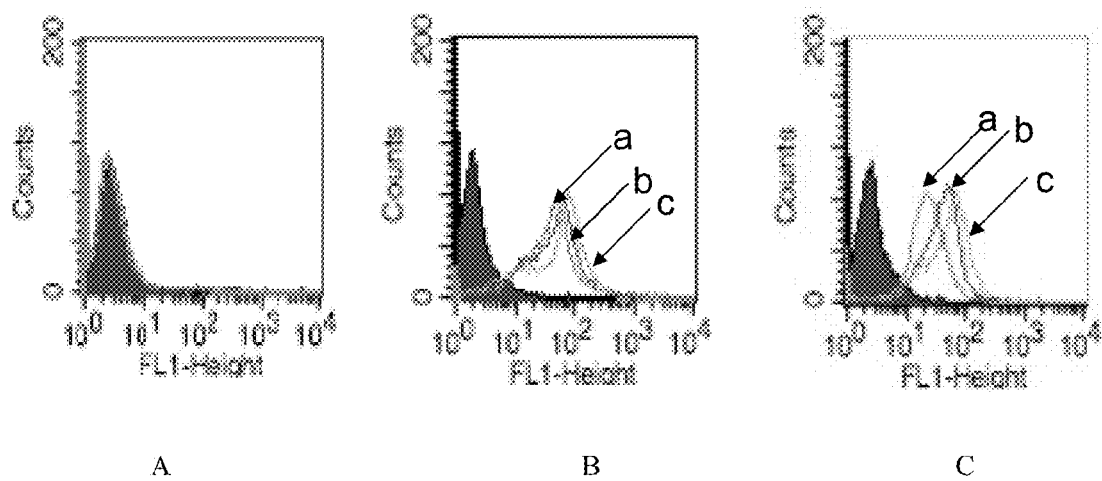
FIG. 3 shows the results of flow cytometry using the reaction of a PPAT-057-17 antibody with each cell line. A: CHO cells, B: CDH3 forced expression CHO cells, and C: lung cancer-derived cell line NCI-H358. a: 0.01 µg/ml anti-CDH3 antibody, b: 0.1 µg/ml anti-CDH3 antibody, and c: 1 µg/ml anti-CDH3 antibody.

The results of typical reactions of the antibody PPAT-057-17 obtained from the aforementioned hybridomas with CDH3-expressing CHO cells (EXZ1501), with CHO cells as a parent cell line, and with cancer cells NCI-H358 that had been confirmed to express CDH3 at a high level, are shown in FIG. 3.

Example 4

Figure 4:
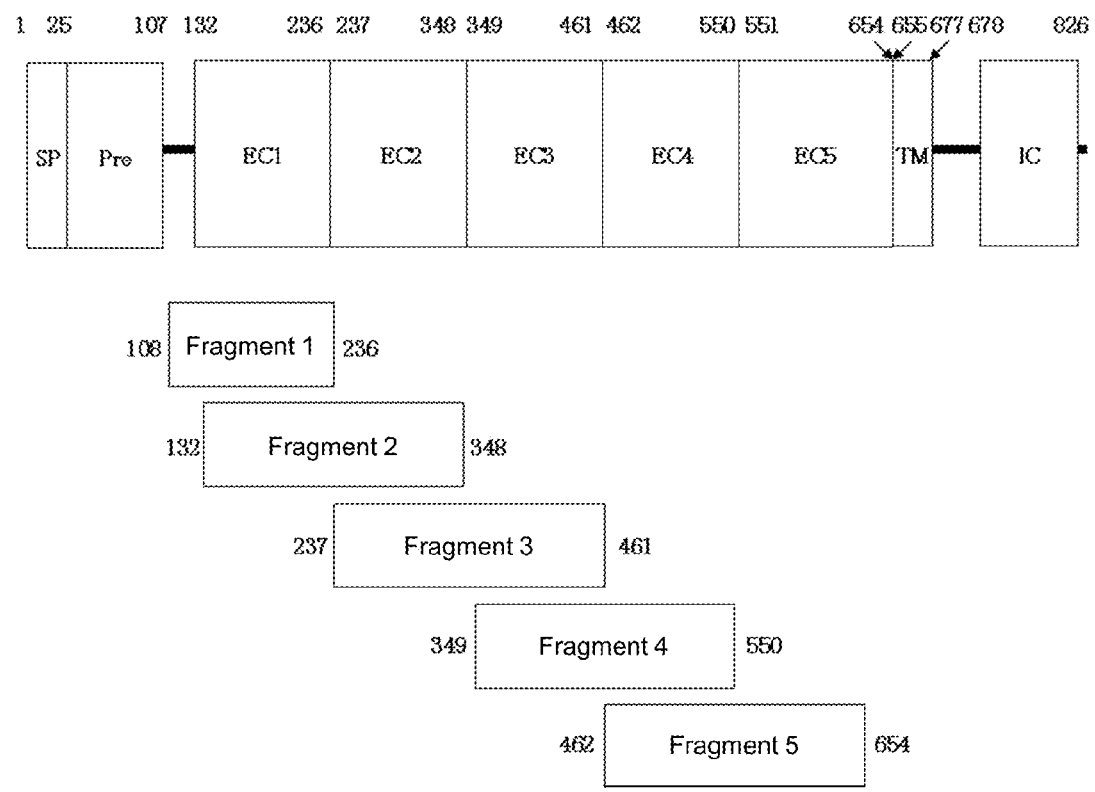
FIG. 4 shows the correspondence of CDH3 protein fragments 1 to 5 with a CDH3 extracellular region.

Identification of Recognition Site of Anti-CDH3 Monoclonal Antibody Using CDH3 Protein Fragments The recognition site of the anti-CDH3 antibody was identified by a Western blot method with CDH3 protein fragments. Fragments 1 to 5 were designed, so that the sequences of individual CDH3 fragments could be sufficiently overlapped (FIG. 4).

(1) Construction of Expression Vector for CDH3 Protein Fragments

Using the full-length CDH3 cDNA of Example 1 as a template, a PCR reaction was carried out employing the aftermentioned primer sets. Using iProof High Fidelity DNA Polymerase (Bio-Rad), the reaction was carried out under reaction conditions consisting of 35 cycles of 98° C.—10 seconds, 60° C.—10 seconds, and 72° C.—30 seconds. Thereafter, gel containing a band with a size near the size of interest was cut out in agarose gel electrophoresis, and using QIA (registered trademark) Quick Gel Extraction Kit, a CDH3 cDNA fragment of interest was obtained.

In order to insert this CDH3 cDNA fragment into an *Escherichia coli* expression vector pCold (registered trademark) TF (TAKARA BIO INC.), the fragment was digested with two types of restriction enzymes KpnI and XbaI, and it was then inserted into pCold TF that has also been digested with KpnI and XbaI according to an ordinary method using T4 DNA ligase, so as to obtain an expression vector for expressing each fragment.

Using the following primer sets, PCR reactions were carried out, so as to obtain individual fragments.

Fragment 1 (positions 108 to 236 of SEQ ID NO: 38)

```
Forward primer:
                                    (SEQ ID NO: 41)
TATGGAGCTCGGTACCGATTGGGTGGTTGCTCCAATATCTG Reverse primer:
                                    (SEQ ID NO: 42)
AGATTACCTATCTAGACTACTGCATCACAGAAGTACCTGGTAGG
```

Fragment 2 (positions 132 to 348 of SEQ ID NO: 38)

```
Forward primer.
                                             (SEQ ID NO: 43)
TATGGAGCTCGGTACCAAGTCTAATAAAGATAGAGACACCAAG Reverse primer:
                                             (SEQ ID NO: 44)
AGATTACCTATCTAGACTACCTCTGCACCTCATGGCCCACTGCATTCTCA
```

Fragment 3 (positions 237 to 461 of SEQ ID NO: 38)

```
    Forward primer.
                                             (SEQ ID NO: 45)
    TATGGAGCTCGGTACCGTGACAGCCACGGATGAGGATGATG Reverse primer:
                                             (SEQ ID NO: 46)
    AGATTACCTATCTAGACTAGACACACACAGGCTCCCCAGTG
```

Fragment 4 (positions 349 to 550 of SEQ ID NO: 38)

```
Forward primer:
                                             (SEQ ID NO: 47)
TATGGAGCTCGGTACCCTGACGGTCACTGATCTGGACG Reverse primer:
                                             (SEQ ID NO: 48)
AGATTACCTATCTAGACTAGGGCTCAGGGACTGGGCCATGGTCATTG
```

Fragment 5 (positions 462 to 654 of SEQ ID NO: 38)

```
Forward primer:
                                             (SEQ ID NO: 49)
TATGGAGCTCGGTACCTACACTGCAGAAGACCCTGACAAGG Reverse primer:
                                             (SEQ ID NO: 50)
AGATTACCTATCTAGACTAACCTCCCTTCCAGGGTCCAGGGCAGGTTTCG
```

(2) Expression of CDH3 Protein Fragments

Using an expression vector for expressing each of the CDH3 fragments described in (1) above, *Escherichia coli* Rossetta (registered trademark) 2 (Merck) was transformed according to an ordinary method, and the transformant was then cultured in an LB medium. When the absorbance at 600 nm became 0.4, the culture product was cooled on ice for 30 minutes. Thereafter, the concentration of isopropyl-β-thiogalactopyranoside (IPTG) was set at 0.5 mM, and the cells were then cultured at 20° C. for 18 hours. Thereafter, the resultant was then recovered.

The expression of CDH3 protein fragments was confirmed by electrophoresing the culture solution of the *Escherichia coli*, then subjecting the resultant to a Western blot method using an anti-Penta-His antibody (QIAGEN), and then confirming the presence of a band in a predicted position.

Figure 5:
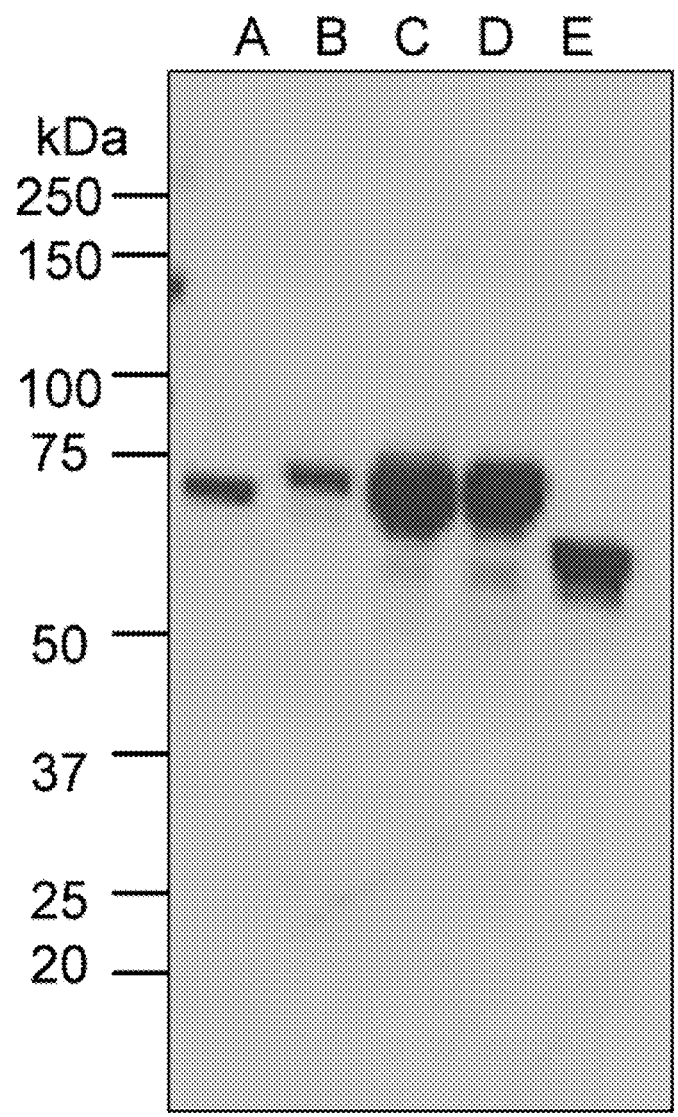
FIG. 5 shows the results regarding the expression of CDH3 protein fragments. A: fragment 1, B: fragment 2, C: fragment 3, D: fragment 4, and F: fragment 5.
Figure 6:
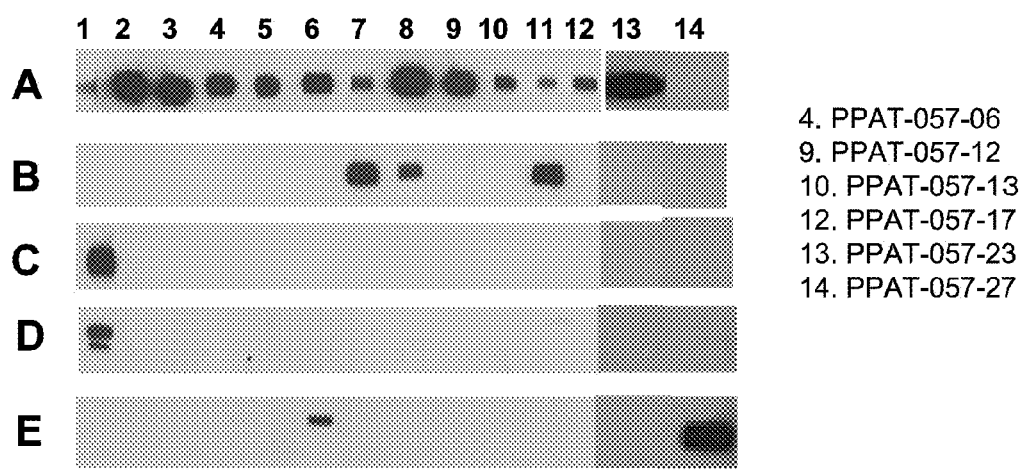
FIG. 6 shows the reaction of CDH3 protein fragments with antibodies according to a Western blotting method. A: fragment 1, B: fragment 2, C: fragment 3, D: fragment 4, and F: fragment 5.

Specifically, an electrophoretic buffer was added to the above-described *Escherichia coli* culture solution in an amount of 1/10 of the culture solution, and the thus mixed solution was then charged to 5%-20% gradient gel (Bio-Rad) under reductive conditions, followed by performing electrophoresis. Thereafter, the resultant was transferred on Immobilon (registered trademark) P membrane (Millipore). The transfer membrane was lightly washed with TBS-T (0.05% Tween (registered trademark) 20, TBS), and it was then shaken in 40% BSA-containing TBS for 1 hour. Thereafter, each anti-CDH3 antibody that had been diluted with TB S-T containing 10% Block Ace (registered trademark) (Snow Brand Milk Products Co., Ltd.) was added to the resultant, and the obtained mixture was then shaken for 1 hour. Thereafter, the reaction product was washed with TBS-T, and a HRP-anti-mouse IgG antibody (GE Healthcare Biosciences) diluted with 10% Block Ace-containing TBS-T was added thereto, followed by shaking the obtained mixture for 1 hour. Subsequently, the reaction product was washed with TBS-T. Using ECL (registered trademark)-Plus (GE Healthcare Biosciences), color development was detected with X-ray film RX-u (Fujifilm Corporation) in accordance with the instructions provided by the manufacturer. The obtained results are shown in FIG. 5.

(3) Identification of Recognition Site of Antibody Using CDH3 Protein Fragments

The above-described *Escherichia coli* lysate, in which each of the above-mentioned CDH3 protein fragments had been expressed, was charged to 5%-20% gradient gel (Bio-Rad) under reductive conditions, followed by performing electrophoresis. Thereafter, using a blotting device (Bio-Rad), the resultant was transferred on Immobilon P membrane (Millipore). The transfer membrane was lightly washed with TBS-T (0.05% Tween 20, TBS), and it was then shaken in 40% BSA-containing TBS for 1 hour. Thereafter, the membrane was cut at equal intervals in the form of straps, and each antibody (including the antibodies PPAT-057-06, PPAT-057-17, PPAT-057-13, PPAT-057-23, PPAT-057-27, and PPAT-057-12) that had been diluted with 10% Block Ace-containing TBS-T was added thereto. The obtained mixture was shaken for 1 hour. Thereafter, the reaction product was washed with TBS-T, and a HRP-anti-mouse IgG antibody (GE Healthcare Biosciences) diluted with 10% Block Ace-containing TBS-T was added thereto, followed by shaking the obtained mixture for 1 hour. Subsequently, the reaction product was washed with TBS-T. Using ECL-Plus (GE Healthcare Biosciences), color development was detected with X-ray film RX-u (Fujifilm Corporation) in accordance with the instructions provided by the manufacturer. As a result, it was found that the antibodies PPAT-057-06, PPAT-057-17, PPAT-057-23, PPAT-057-12, and PPAT-057-13 reacted with Fragment 1 and did not react with Fragments 2 to 5. These results demonstrated that the antibodies PPAT-057-06, PPAT-057-17, PPAT-057-23, PPAT-057-12, and PPAT-057-13 specifically react with an epitope that is present in positions 108 to 131 of the amino acid sequence shown in SEQ ID NO: 38. The antibody PPAT-057-27 did not react with Fragments 1 to 4 and reacted with Fragment 5. Accordingly, it was found that the antibody PPAT-057-27 specifically reacts with an epitope that is present in positions 551 to 654 of the amino acid sequence shown in SEQ ID NO: 38.

Example 5

Production of Chimeric Antibody Against CDH3

Using hybridomas each producing PPAT-057-06, PPAT-057-17, PPAT-057-13, PPAT-057-23, PPAT-057-27, or PPAT-057-12, DNA encoding the variable region of a mouse monoclonal antibody against human CDH3 was cloned as described below. Then, a mouse variable region was connected with the constant region of a human antibody gene, so as to produce chimeric antibodies PPAT-057-06C, PPAT-057-17C, PPAT-057-13C, PPAT-057-23C, PPAT-057-27C, and PPAT-057-12C.

(1) Cloning of Variable Region Gene of Mouse Monoclonal Antibody PPAT-057-17

(i) Purification of RNA from Hybridomas

Cytoplasmic RNA was isolated from hybridoma cells producing PPAT-057-17 (Accession No. NITE BP-865) according to the method described in Gough, Rapid and quantitative preparation of cytoplasmic RNA from small numbers of cells, Analytical Biochemisty, 173, pp. 93-95 (1988) (wherein another TNE buffer (25 mM Tris-HCl, pH 7.5; 1% NP-40; 150 mM NaCl; 1 mM EDTA, pH 8.0) was used, instead of the lysis buffer described in the aforementioned study paper). Specifically, hybridoma cells (5×10⁶) was suspended in 0.2 mL of a TNE buffer to dissolve the cell membrane therein, and the cell nucleus was then removed by centrifugation. To approximately 0.2 mL of the obtained cytoplasm supernatant, 0.2 mL of an extraction buffer (10 mM Tris-HCl, pH7.5; 0.35 M NaCl; 1% (w/v) SDS; 10 mM EDTA, pH 8.0; 7 M urea) was added. The obtained mixture was extracted with phenol and chloroform, and glycogen (Roche; Cat No. 901393) was then added as a carrier to the obtained RNA solution. The reaction mixture was precipitated with ethanol. Subsequently, 10 to 50 µl of sterile distilled water was added to the RNA precipitate, resulting in a cytoplasmic RNA concentration of 0.5 to 2 µg/µl, so that the precipitate was dissolved therein.

(ii) Preparation of cDNA Library from RNA Prepared from Hybridomas

In order to synthesize single-stranded cDNA, 0.5 to 3 µg of the above-prepared cytoplasmic RNA was added to a reaction solution containing 50 mM Tris-HCl, pH 8.3 (room temperature); 75 mM KCl; 3 mM MgCl₂; 10 mM DTT, 100 ng of random primer, 0.5 mM dNTP, and 200 units of Superscript II (reverse transcriptase, Invitrogen) to prepare 20 µL of a reaction mixture, and the reaction mixture was then incubated at 42° C. for 50 minutes. The thus synthesized cDNA library was directly used as a template in a polymerase chain reaction (PCR) method.

(iii) Amplification of Gene Encoding Variable Region of Anti-CDH3 Antibody PPAT-057-17 by PCR Method Primers used in the experiments were all synthesized by Hokkaido System Science Co., Ltd.

(Primers Used to Amplify Gene Encoding Mouse L Chain Variable Region by PCR Method)

Using two types of primer sets, namely, (1) a DNA primer having homology with a FR1 portion at the 5'-terminus, and 4 primer sets having homology with a J chain gene in a mouse L chain at the 3'-terminus, and (2) primer sets having homology with an L chain signal portion at the 5'-terminus (7 primer sets), and a primer with a KC portion at the 3'-terminus (KVL antisense primer), mouse immunoglobulin L chain variable region DNA was isolated from the cDNA by a polymerase chain reaction, and the sequence of the obtained gene was then analyzed. The amino acid sequence of an L chain variable region was obtained from this gene (SEQ ID NO: 51). The primer sequences are as follows.

(4 Sense Primer Sets for Cloning of Mouse L Chain Variable Region)

With reference to "Phage Display—A Laboratory Manual—, Barbas Burton Scott Silverman" PROTOCOL 9.5, 17 types of sense primers and 3 types of reverse primers were synthesized by Hokkaido System Science Co., Ltd.

VK sense (FR1 portion): A mixture of the following 17 primers was used as a VK sense primer.

```
                                         SEQ ID NO: 52
5'-GAYATCCAGCTGACTCAGCC-3'  (Degeneracy: 2)

SEQ ID NO: 53
5'-GAYATTGTTCTCWCCCAGTC-3'  (Degeneracy: 4)

SEQ ID NO: 54
5'-GAYATTGTGMTMACTCAGTC-3'  (Degeneracy: 8)

SEQ ID NO: 55
5'-GAYATTGTGYTRACACAGTC-3'  (Degeneracy: 8)

SEQ ID NO: 56
5'-GAYATTGTRATGACMCAGTC-3'  (Degeneracy: 8)

SEQ ID NO: 57
5'-GAYATTMAGATRAMCCAGTC-3'  (Degeneracy: 16)

SEQ ID NO: 58
5'-GAYATTCAGATGAYDCAGTC-3'  (Degeneracy: 12)

SEQ ID NO: 59
5'-GAYATYCAGATGACACAGAC-3'  (Degeneracy: 4)

SEQ ID NO: 60
5'-GAYATTGTTCTCAWCCAGTC-3'  (Degeneracy: 4)

SEQ ID NO: 61
5'-GAYATTGWGCTSACCCAATC-3'  (Degeneracy: 8)

SEQ ID NO: 62
5'-GAYATTSTRATGACCCARTC-3'  (Degeneracy: 16)

SEQ ID NO: 63
5'-GAYRTTKTGATGACCCARAC-3'  (Degeneracy: 16)

SEQ ID NO: 64
5'-GAYATTGTGATGACBCAGKC-3'  (Degeneracy: 12)

SEQ ID NO: 65
5'-GAYATTGTGATAACYCAGGA-3'  (Degeneracy: 4)

SEQ ID NO: 66
5'-GAYATTGTGATGACCCAGWT-3'  (Degeneracy: 4)

SEQ ID NO: 67
5'-GAYATTGTGATGACACAACC-3'  (Degeneracy: 2)

SEQ ID NO: 68
5'-GAYATTTTGCTGACTCAGTC-3'  (Degeneracy: 2)
```

J antisense (4 primer sets)

```
J1/J2 antisense primer (1)
                                         SEQ ID NO: 69
5'-GGSACCAARCTGGAAATMAAA-3'  (Degeneracy: 8)

J4 antisense primer (2)
                                         SEQ ID NO: 70
5'-GGGACAAAGTTGGAAATAAAA-3'

J5 antisense primer (3)
                                         SEQ ID NO: 71
5'-GGGACCAAGCTGGAGCTGAAA-3'
```

A mixture of J1/J2, J4, and J5 antisense primers (4)

(7 Primer Sets for Cloning of Mouse L Chain Variable Region)

VK Sense (Signal Peptide Portion)

These primers were prepared by modifying nucleotide sequences based on the Mouse Ig-Primer Set of Novagen (Novagen; Merck, Cat No. 69831-3), such that restriction sites were removed.

Sense primer set A

```
                                         SEQ ID NO: 72
5'-ATGRAGWCACAKWCYCAGGTCTTT-3'
```

Sense primer set B

```
                                         SEQ ID NO: 73
5'-ATGGAGACAGACACACTCCTGCTAT-3'
```

Sense primer set C

SEQ ID NO: 74
5'-ATGGAGWCAGACACACTSCTGYTATGGGT-3'

Sense primer set D (a mixture of the following two types of primers was used)

SEQ ID NO: 75
5'-ATGAGGRCCCCTGCTCAGWTTYTTGGIWTCTT-3'

SEQ ID NO: 76
5'-ATGGGCWTCAAGATGRAGTCACAKWYYCWGG-3'

Sense primer set E (a mixture of the following three types of primers was used)

SEQ ID NO: 77
5'-ATGAGTGTGCYCACTCAGGTCCTGGSGTT-3'

SEQ ID NO: 78
5'-ATGTGGGGAYCGKTTTYAMMCTTTTCAATTG-3'

SEQ ID NO: 79
5'-ATGGAAGCCCCAGCTCAGCTTCTCTTCC-3'

Sense primer set F (a mixture of the following four types of primers was used)

SEQ ID NO: 80
5'-ATGAGIMMKTCIMTTCAITTCYTGGG-3'

SEQ ID NO: 81
5'-ATGAKGTHCYCIGCTCAGYTYCTIRG-3'

SEQ ID NO: 82
5'-ATGGTRTCCWCASCTCAGTTCCTTG-3'

SEQ ID NO: 83
5'-ATGTATATATGTTTGTTGTCTATTTCT-3'

Sense primer set G (a mixture of the following four types of primers was used)

SEQ ID NO: 84
5'-ATGAAGTTGCCTGTTAGGCTGTTGGTGCT-3'

SEQ ID NO: 85
5'-ATGGATTTWCARGTGCAGATTWTCAGGTT-3'

SEQ ID NO: 86
5'-ATGGTYCTYATVTCCTTGCTGTTCTGG-3'

SEQ ID NO: 87
5'-ATGGTYCTYATVTTRCTGCTGCTATGG-3'

KVL Antisense Primer

SEQ ID NO: 88:  5'-ACTGGATGGTGGGAAGATGGA-3'

(Primers Used to Amplify Gene Encoding Mouse H Chain Variable Region by PCR Method)

Using a primer having homology with a mouse H chain signal portion (4 primer sets) at the 5'-terminus and a primer having homology with a KC portion at the 3'-terminus, or using 1 primer set having homology with a FR1 portion at the 5'-terminus and two types of primer sets having homology with the constant region of a mouse H chain (IGHC) at the 3'-terminus, mouse immunoglobulin H chain variable region DNA was isolated from the cDNA by a polymerase chain reaction, and the sequence of the obtained gene was then analyzed. The amino acid sequence of an H chain variable region was obtained from this gene (SEQ ID NO: 89). The primer sequences are as follows.

Primers for Cloning of Mouse H Chain Variable Region
VH Sense (Signal Portion: 4 Primer Sets)

These primers were designed with reference to Table 2.12.2 shown in Current Protocols in Immunology (John Wiley and Sons, Inc.), Unit 2.12 Cloning, Expression, and Modification of Antibody V Regions.

SEQ ID NO: 90
5'-ATGGRATGSAGCTGKGTMATSCTCTT-3' (Degeneracy: 32)

SEQ ID NO: 91
5'-ATGRACTTCGGGYTGAGCTKGGTTTT-3' (Degeneracy: 8)

SEQ ID NO: 92
5'-ATGGCTGTCTTGGGGCTGCTCTTCT-3'

SEQ ID NO: 93
5'-ATGGRCAGRCTTACWTYY-3' (Degeneracy: 32)

Primers for Cloning of Mouse H Chain Variable Region
VH Sense (FR1 Portion)

This primer was designed by modifying the nucleotide sequence of the sense primer described in Tan et al., "Superhumanized" Antibodies: Reduction of Immunogenic Potential by Complementarity-Determining Region Grafting with Human Germline Sequences: Application to an Anti-CD281, Journal of Immunology 169 (2002) pp. 1119-1125.

SEQ ID NO: 94
5'-SAGGTSMARCTKSAGSAGTCWGG-3' (Degeneracy: 256)

VH Antisense (Antisense Primer Common in 3 and 4)

This primer was designed by degenerating the nucleotide sequence such that it can anneal with all isoforms of mouse IgG SEQ ID NO: 95
5'-CASCCCCATCDGTCTATCC-3' (Degeneracy: 6)

(2) Construction of Transient Expression Vector for Chimeric Antibody PPAT-057-17C
Construction of Expression Plasmid:

Using the primers shown in SEQ ID NOS: 52 to 95, a variable region in each of the L chain and H chain of an anti-CDH3 mouse monoclonal antibody PPAT-057-17 was amplified by a PCR method employing DNA Engine (Peltier Thermal Cycler, MJ Research, Bio-Rad). The amplified DNA fragment was inserted into a subcloning vector p-GEM (Promega), and the nucleotide sequence thereof was then determined using T7 and SP6 universal primers for this vector.

The nucleotide sequence of a variable region in each of the L chain and H chain of a chimeric anti-CDH3 antibody was searched on the IMGTN-QUEST Search page (http://imgt.cines.fr/IMGT_vquest/vquest?livret=0&Option=mouseIg). As a result, it was confirmed that the antibody gene could be reliably cloned.

CDR1 in the heavy chain variable region (VH) of the aforementioned chimeric anti-CDH3 antibody comprised the amino acid sequence shown in SEQ ID NO: 1; CDR2 in the heavy chain variable region (VH) thereof comprised the amino acid sequence shown in SEQ ID NO: 2; CDR3 in the heavy chain variable region (VH) thereof comprised the amino acid sequence shown in SEQ ID NO: 3; CDR1 in the light chain variable region (VL) thereof comprised the amino acid sequence shown in SEQ ID NO: 4; CDR2 in the light chain variable region (VL) thereof comprised the amino acid sequence shown in SEQ ID NO: 5; and CDR3 in the light chain variable region (VL) thereof comprised the amino acid sequence shown in SEQ ID NO: 6.

By applying the same method as described above, antibody variable regions were each cloned from the hybridomas of PPAT-057-06, PPAT-057-13, PPAT-057-23, PPAT-057-27, and PPAT-057-12. As a result, it was found that the CDR1, CDR2 and CDR3 of the PPAT-057-06C heavy chain variable region (VH) comprise the amino acid sequences shown in SEQ ID NO: 7, 8 and 9, respectively, and that the CDR1, CDR2 and CDR3 of the PPAT-057-06C light chain variable region (VL) comprise the amino acid sequences shown in SEQ ID NO: 10, 11 and 12, respectively. It was also found that the CDR1, CDR2 and CDR3 of the PPAT-057-13C heavy chain variable region (VH) comprise the amino acid sequences shown in SEQ ID NO: 13, 14 and 15, respectively, and that the CDR1, CDR2 and CDR3 of the PPAT-057-13C light chain variable region (VL) comprise the amino acid sequences shown in SEQ ID NO: 16, 17 and 18, respectively. It was also found that the CDR1, CDR2 and CDR3 of the PPAT-057-23C heavy chain variable region (VH) comprise the amino acid sequences shown in SEQ ID NO: 19, 20 and 21, respectively, and that the CDR1, CDR2 and CDR3 of the PPAT-057-23C light chain variable region (VL) comprise the amino acid sequences shown in SEQ ID NO: 22, 23 and 24, respectively. It was also found that the CDR1, CDR2 and CDR3 of the PPAT-057-27C heavy chain variable region (VH) comprise the amino acid sequences shown in SEQ ID NO: 25, 26 and 27, respectively, and that the CDR1, CDR2 and CDR3 of the PPAT-057-27C light chain variable region (VL) comprise the amino acid sequences shown in SEQ ID NO: 28, 29 and 30, respectively. It was further found that the CDR1, CDR2 and CDR3 of the PPAT-057-12C heavy chain variable region (VH) comprise the amino acid sequences shown in SEQ ID NO: 31, 32 and 33, respectively, and that the CDR1, CDR2 and CDR3 of the PPAT-057-12C light chain variable region (VL) comprise the amino acid sequences shown in SEQ ID NO: 34, 35 and 36, respectively.

Subsequently, genes each encoding the V regions of the L chain and H chain of the cloned anti-PPAT-057-17 antibody were prepared by designing a gene, in which a gene encoding a human Ck region was ligated to a chimeric L chain expression vector and a gene encoding a human Cg1 region was ligated to a chimeric H chain expression vector, and then performing the artificial synthesis of the thus designed, full-length L chain and H chain chimeric antibody genes by GenScript. Upon the artificial synthesis of the full-length genes, optimization of codon usage was carried out for the advantages of gene expression in CHO-producing cells (in accordance with the method described in Kim et al., Codon optimization for high-level expression of human erythropoietin (EPO) in mammalian cells, Gene, Vol. 199, 1997, pp. 293-301). Specifically, in the case of the L chain, a DNA sequence essential for efficient translation (Kozak, M., J., At least six nucleotides preceding the AUG initiator codon enhance translation in mammalian cells. J. Mol. Biol. 196, pp. 947-950, 1987), a signal peptide of a mouse IGKV (k chain variable region) gene, a V region of the L chain of an anti-CDR3 antibody, and human KC (k chain constant region) were aligned in this order, and restriction enzyme sites (NheI on the 5'-terminal side and EcoRI on the 3'-terminal side) were then added to the both termini. A chimeric H chain was produced in the same manner as described above. The thus produced artificial synthetic genes were cleaved with NheI and EcoRI, and the gene fragments were then inserted into the NheI and EcoRI sites of the expression vector pCAGGS, so as to obtain an expression vector pCAGGS-IGK for an anti-CDH3 chimeric antibody L chain, and an expression vector pCAGGS-IGH for an anti-CDH3 chimeric antibody H chain.

(3) Construction of Stable Expression Vector for Chimeric Antibody PPAT-057-17C

To allow a recombinant antibody gene to express at a high level in CHO cells, an expression vector was constructed by ligating the antibody gene to a CMV promoter sequence and inserting a dihydrofolate reductase (dhfr) gene having a poly (A) signal into the vector.

To produce a cell line capable of stably expressing and producing a chimeric antibody, a pCAGGS expression vector, into which a dhfr gene was inserted, was constructed. Specifically, a CMV promoter and a dgfr gene having a poly(A) signal were inserted into transient expression vectors pCAGGS-IGH and pCAGGS-IGK A CMV promoter, a mouse dgfr gene having a Kozak sequence, and a SV40 poly(A) signal were each amplified according to a PCR method. Thereafter, the mixture of these genes were ligated with one another by the PCR method, and at the same time, HindIII sites were added to both termini, so as to obtain a gene fragment HindIII-CMV promoter-Kozak-dhfr-poly(A)-HindIII. This fragment was inserted into the HindIII site of pCAGGS-IGH or pCAGGS-IGK to obtain pCAGGS-IGH-CMVp-dhfr-A and pCAGGS-IGK-CMVp-dhfr-A. These expression vectors can express chimeric antibody by a CAG promote; and can express dgfr gene by a CMV promoter, and thus, they could efficiently produce chimeric antibodies by utilizing gene amplification.

(4) Establishment of CHO Cell Line Capable of Producing Chimeric Antibody PPAT-057-17C CHO dhfr(–) cells (G Urlaub et al., Isolation of Chinese hamster cell mutants deficient in dihydrofolate reductase activity, Proc. Natl. Acad. Sci. USA 77, pp. 4216-4220, 1980) were used in simultaneous transformation with two types of plasmids (wherein a plasmid was cleaved with PvuI in an ampicillin resistance gene to form linear plasmids from a cyclic plasmid), namely, with a pCAGGS-IGK-CMV-dhfr-A vector used for expression of a chimeric anti-CDH3 L chain and a pCAGGS-IGH-CMV-dhfr-A vector used for expression of a chimeric anti-CDH3 H chain. Electroporation was carried out using Amaxa manufactured by LONZA. DNA (0.002 mg/sample of each plasmid for the L chain and the H chain) was added to 0.1 mL of Amaxa electroporation CHO buffer containing 3×10e3 cells, and electric pulse was then given thereto.

The cells treated by electroporation were added to an Iscove's Modified Dulbecco Medium (IMDM), which contained 10% dialyzed FBS and did not contain HT (H: hypoxanthine; T: thymidine). Three days after the gene transfection, the medium was replaced with IMDM which contained 10% dialyzed FBS and 2 mM L-glutamine, and did not contain HT. Thereafter, the transfected neo+ cells were selected with 1 mg/mL G418, and clones of a chimeric antibody production-positive cell line were obtained. Subsequently, gene amplification was carried out using the clones selected with G418. The gene was amplified in 2 rounds of methotrexate (MTX) (0.25 mM, 1 mM), and a cell line capable of producing approximately 50 to 100 mg of chimeric CDH3 antibody per liter could be established.

Cell lines each capable of producing chimeric antibodies PPAT-057-06C, PPAT-057-13C, PPAT-057-23C, PPAT-057-27C, and PPAT-057-12C were established by the same method as described above.

(5) Quantification of Chimeric Antibody by Enzyme-Linked Immunosorbent Assay (ELISA)

A culture supernatant of the transfected CHO cells was measured by ELISA, and it was confirmed that a chimeric antibody had been produced. To detect the chimeric antibody, a plate was coated with goat anti-human IgG (H+L) (which had previously been absorbed against mouse, rabbit, bovine, and mouse IgG) (COSMO BIO: AQI, Cat No. A-110UD). After blocking, the culture supernatant obtained from CHO cells capable of producing anti-CDH3 chimeric antibody was subjected to serial dilution, and was then added to each well. After the plate had been subjected to incubation and washing, goat anti-human IgG (H+L) (which had previously been absorbed against mouse, rabbit, bovine, and mouse IgG)-HRP(COSMO BIO: AQI, Cat No. A-110UD) was added to the plate. Following incubation and washing, a substrate buffer was added to the plate. Incubation was further carried out, the reaction was then terminated, and the absorbance at 450 nm was then measured. Purified human IgG was used as a standard.

Example 6

Measurement of Antigen-Binding Activity of Chimeric Antibody PPAT-057-17C

The antigen-binding activity of the purified chimeric antibody PPAT-057-17C was measured by flow cytometry, using a CHO cell line (EXZ1501) expressing full-length CDH3 or a CDH3-positive expression lung cancer cell line NCI-H358.

Figure 7:
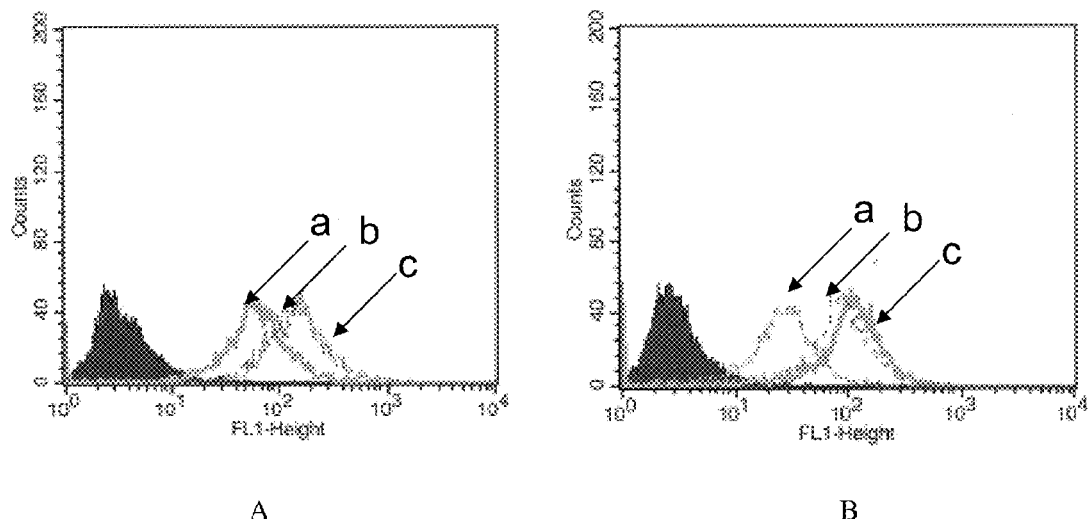
FIG. 7 shows the results of flow cytometry using the reaction of the chimeric antibody PPAT-057-17C with each cell line. A: CDH3 forced expression CHO cells, and B: lung cancer-derived cell line NCI-H358. a: 0.1 µg/ml anti-CDH3 antibody, b: 1 µg/ml anti-CDH3 antibody, and c: 10 µg/ml anti-CDH3 antibody.

Each cell line was treated with 2 mM EDTA-PBS to remove the cells from a culture plate, and the cells were then suspended in a FACS solution at $1 \times 10^6$ cell/mL. This cell suspension was inoculated on a 96-well plate at 50 µL/well, and the purified chimeric antibody PPAT-057-17C was then added in each different concentrations to the plate, followed by performing a reaction at 4° C. for 60 minutes. Thereafter, the wells were washed with a FACS solution (200 µL/well) two times, and 4 µg/ml AlexaFlour488-labeled anti-human IgG/goat F(ab')$_2$ (Invitrogen) was then added to the resultant. The obtained mixture was reacted at 4° C. for 30 minutes. Thereafter, the reaction mixture was washed with a FACS solution two times, and was then subjected to flow cytometry. As a result, as shown in FIG. 7, the chimeric antibody PPAT-057-17C was found to have strong reactivity with a CDH3-expressing cell line.

Example 7

Measurement of Antibody-Dependent Cellular Cytotoxicity (ADCC) of Chimeric Antibody PPAT-057-17C ADCC activity was measured using EuTDA cytotoxicity assay kits (PerkinElmer, Cat. AD0116).
(1) Preparation of Effector Cells Bone marrow cells were collected from the femur of a C3H/HeJ Jcl mouse (8-week-old, male, CLEA Japan, Inc.), and were adjusted at $2 \times 10^6$ cells/mL in a 10% FBS-containing RPMI1640 medium. The cells were cultured in the presence of 50 mg/mL human IL-2 (PEPROTECH) and 10 ng/mL mouse GM-CSF (PEPROTECH) for 6 days. On the day of performing measurement, the cells were recovered, and were then washed with a 10% FBS-containing RPMI1640 medium, so as to obtain a solution of effector cells.

(2) Preparation of Target Cells

A CDH3-positive expression lung cancer cell line NCI-H358 was used as target cells. The cells were removed from a plate, and were then suspended in a 10% FBS-containing RPMI1640 medium at $1 \times 10^6$ cells/mL. Then, 5 µl/ml BATDA was added to the suspension, and the obtained mixture was then cultured at 37° C. for 25 minutes. Thereafter, the resulting cells were washed with a medium four times, and a 10% FBS-containing RPMI1640 medium was then added to the resultant. The resulting cells were inoculated on a 96-well U-bottom plate (NUNC) at $1 \times 10^4$ cells/well, so as to prepare target cells.
(3) Measurement of ADCC Activity An antibody solution (the antibody PPAT-057-17 or the chimeric antibody PPAT-057-17C) that had been adjusted to a concentration of 0.01, 0.1, or 1 µg/mL was dispensed at 50 µL/well into each well that contained the target cells, and the mixture was then incubated at room temperature for 15 minutes. Subsequently, 100 µL of effector cells ($4 \times 10^5$ cells/well) was dispensed into each well, and the obtained mixture was then cultured in a carbon dioxide incubator for 3 hours. Thereafter, a culture supernatant was recovered, and 20 µL of the culture supernatant was transferred on a fluorescence measurement plate. Then, 100 µl of an Eu solution was added, and the obtained mixture was then reacted at room temperature for 15 minutes. Thereafter, the amount of fluorescence in each well of the plate was measured using a fluorescence plate reader.

Herein, cytotoxicity was obtained according to the following formula:

$$\text{Cytotoxicity}(\%) = (A-C)/(B-C) \times 100$$

Figure 8:
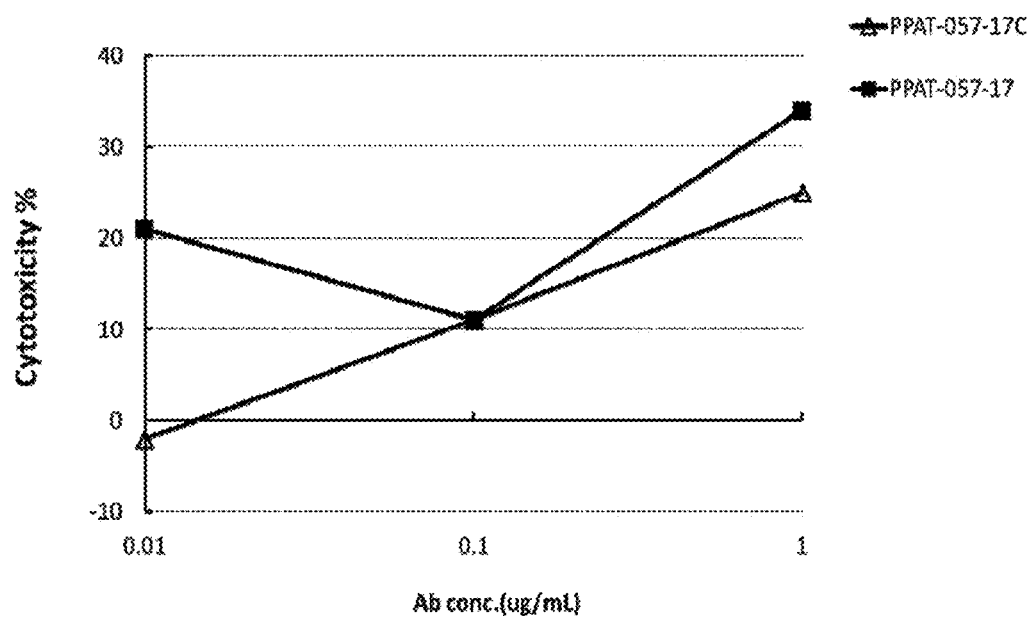
FIG. 8 shows the in vitro ADCC activity of the antibody PPAT-057-17 and that of the chimeric antibody PPAT-057-17C.

A: The amount of fluorescence in each antibody-added well
B: The amount of fluorescence in a well, in which 100 µL of 2% NP40 solution and 50 µL of 10% FBS-containing RPMI medium were added to the target cells
C: The amount of fluorescence in a well, which 150 µL of 10% FBS-containing medium that contained effector cells was added to the target cells Using the aforementioned formula, the ADCC activity was calculated. The results are shown in FIG. 8.

Example 8

Measurement of Antibody-Dependent Cellular Cytotoxicity (ADCC) of Chimeric Antibody ADCC activity was measured, using a bladder cancer cell line BFTC905 as target cells and mouse bone marrow cells as effector cells, and employing a kit manufactured by PROMEGA, CytoTox96 non-Radioactive Cytotoxicity Assay.
(1) Preparation of Effector Cells Bone marrow cells were collected from the femur of a C.B-17/Icr-scid mouse (8-week-old, male, CLEA Japan, Inc.), and were then cultured for 6 days in a 10% FBS-containing RPMI1640 medium supplemented with 50 ng/mL recombinant human IL-2 (PEPROTECH) and 10 ng/mL recombinant mouse GM-CSF (PEPROTECH). The bone marrow cells were recovered on the day of measurement, and were then adjusted at $0.9 \times 10^7$ cells/mL with a measurement buffer (a 2.5% FBS-containing RPMI1640 medium that did not contain phenol red), so as to prepare a solution of effector cells.
(2) Preparation of Target Cells A CDH3-positive expression bladder cancer cell line BFTC905 was used as target cells. The cells were removed from a plate, and were then suspended in a 10% FBS-containing RPMI1640 medium at $0.75 \times 10^5$ cells/mL. Thereafter, the suspension was dispensed at 100 μL/well into a 96-well U-bottom plate. On the following day, the reaction mixture was washed with a measurement buffer (a 2.5% FBS-containing RPMI1640 medium that did not contain phenol red), and a measurement buffer was added at 50 μL/well to the plate.

(3) Measurement of ADCC Activity

Figure 9:
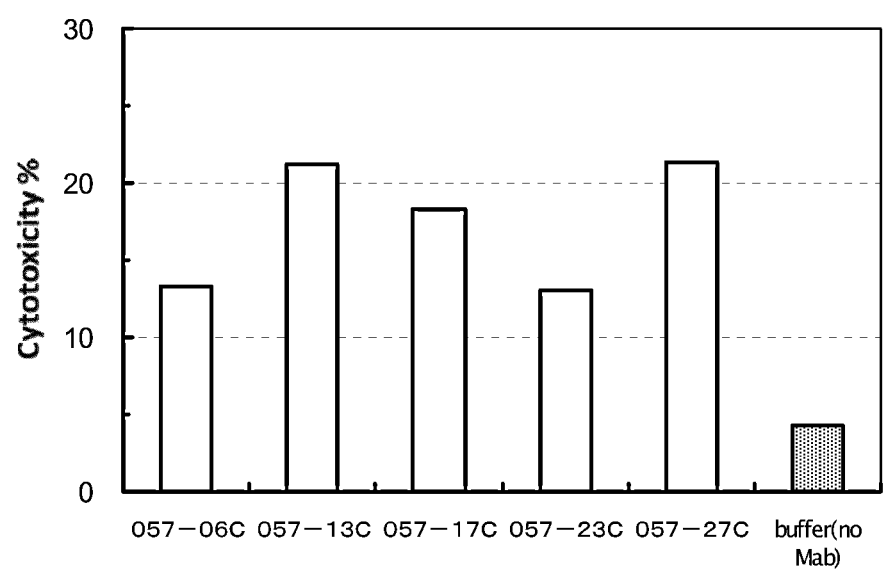
FIG. 9 shows the in vitro ADCC activity of each chimeric antibody.

An antibody solution was adjusted to 12 μg/mL with a measurement buffer, and it was then added at 25 μL/well to a plate, on which the target cells had been dispersed. The obtained mixture was left in a 5% $CO_2$ incubator for 30 minutes. Thereafter, the prepared effector cells were added at 25 μL/well to the plate (final antibody concentration: 3 μg/mL; effector cells: target cells=31:1). The obtained mixture was left at 37° C. in a 5% $CO_2$ incubator for 4 hours. Thereafter, a 50 μL/well supernatant was recovered, and was then subjected to a measurement using CytoTox96 non-Radioactive Cytotoxicity Assay. The results are shown in FIG. 9.

Example 9

Antitumor Effects of Chimeric Antibody PPAT-057-17C on Xenograft Models

The antitumor effects of the chimeric antibody PPAT-057-17C were confirmed using xenograft models, into which a human lung cancer-derived cell line NCI-H358 had been transplanted.

NCI-H358 was cultured in a 10% FBS-containing RPMI1640 medium, and the thus obtained cell culture was then transplanted into the subcutis on the right abdomen of each SCID mouse (female, 7-week-old, CLEA Japan, Inc.) at $5 \times 10^6$ cells/mouse.

The NCI-H358-transplanted mice were divided into four groups (n=8). With regard to each group, the antibody PPAT-057-17 or the chimeric antibody PPAT-057-17C was administered at an amount of 0.3 mg/kg, 1.5 mg/kg, or 7.5 mg/kg into the caudal vein of each mouse. With regard to a negative control group, PBS was administered at an amount of 0.2 mL/20 g into the caudal vein of each mouse. Administration was initiated at the time point at which the mean tumor volume reached 80 $mm^3$, and was carried out two times a week (every three or four days) in a total of eight times.

Figure 10:
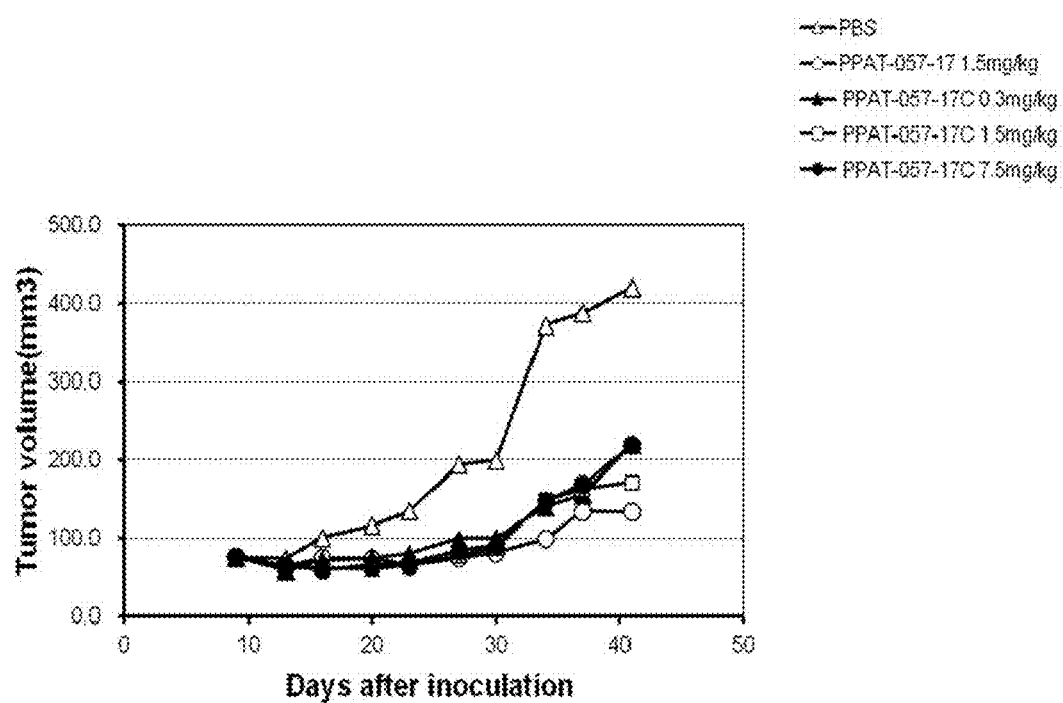
FIG. 10 shows the in vivo antitumor effects of the antibody PPAT-057-17 and those of the chimeric antibody PPAT-057-17C.

On the day of administration, tumor size and body weight were measured. After completion of the final administration, the mice were further observed for 1 week, and then, body weight, tumor volume and tumor weight were measured. The results are shown in FIG. 10. The results of the antibody administration groups were compared with the results of the PBS administration group. As a result, the chimeric antibody PPAT-057-17C was found to exhibit antitumor effects in all of the antibody administration groups.

Example 10

In Vivo Tumor Growth-Suppressing Effect of $F(Ab')_2$ (1) Preparation of $F(ab')_2$ The antibody PPAT-057-17 or a negative control antibody was dialyzed against a dialysis buffer (5 mM Tris-HCl, 150 mM NaCl, pH 7.5) overnight, and it was then adjusted to a final concentration of 5 mg/ml. Subsequently, the same volume of digestion buffer (0.2 M Sodium citrate buffer, pH 4) was added to the solution, and 0.25 mg/ml Pepsin (Roche) was further added thereto. Thus, the obtained mixture was digested with pepsin at 37° C. for 2 hours. Thereafter, 2M Tris-HCl buffer (pH 8.2) that was in a volume of 1/10 of the reaction solution was added to the reaction solution to terminate the pepsin digestion reaction, and $F(ab)_2$ was then purified by gel filtration. Finally, the buffer was replaced with another buffer (20 mM $Na_2PO_4$. $2H_2O$, 150 mM NaCl), and endotoxin was then removed using Mustang E membrane (Pall life sciences, Port Washington, N.Y.). As a result of performing high performance liquid chromatography (HPLC) and SDS-PAGE, the purity of the purified $F(ab')_2$ was found to be 99% or more (FIGS. 11A and B).

(2) In Vivo Tumor Growth-Suppressing Effect of $F(Ab')_2$

NCI-H358 was cultured in a 10% FBS-containing RPMI1640 medium, and the culture was then transplanted in the subcutis on the right abdomen of each SCID mouse (female, 7-week-old, CLEA Japan, Inc.) at $5 \times 10^6$ cells/mouse.

The NCI-H358-transplanted mice were divided into four groups (n=8). Taking into consideration a difference in half-life between IgG antibody and F(ab')2, the antibody PPAT-057-17 IgG or a negative control antibody IgG was administered at an amount of 1.5 mg/kg into the caudal vein of each mouse in each group, or the PPAT-057-17 $F(ab')_2$ or the negative control $F(ab')_2$ was administered at an amount of 1 mg/kg into the caudal vein of each mouse in each group. Administration was initiated at the time point at which the mean tumor volume reached 100 $mm^3$. The IgG antibody was administered two times a week in a total of eight times. On the other hand, the $F(ab')_2$ was administered three times a week in a total of twelve times.

Figure 11C:
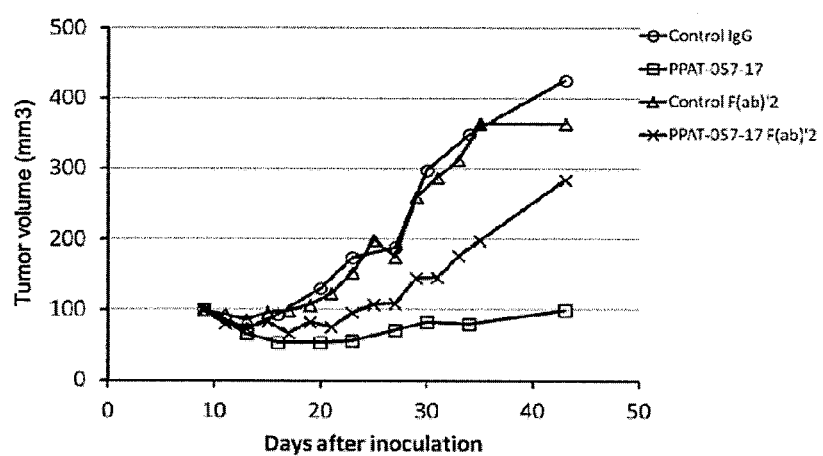
FIG. 11 shows the purity (A,B) and in vivo tumor growth-suppressing effect (C) of F(ah')2. A: High performance liquid chromatography (HPLC); B: SDS-PAGE; and C: the in vivo tumor growth-suppressing effect of F(ab')2 derived from the antibody PPAT-057-17.

On the day of administration, tumor size and body weight were measured. After completion of the final administration, the body weight, the tumor volume and the tumor weight were measured. The results are shown in FIG. 11C. When compared with the negative control $F(ab')_2$ administration group, the $F(ab')_2$ of the antibody PPAT-057-17 exhibited a tumor growth-suppressing effect. These results demonstrated that the antibody PPAT-057-17 has an ADCC-non-dependent tumor growth-suppressing action.

Example 11

Antitumor Effects of Chimeric Antibody PPAT-057-27C on Xenograft Models

The antitumor effects of the chimeric antibody PPAT-057-27C were confirmed using xenograft models, into which a human bladder cancer-derived cell line BFTC905 had been transplanted.

The bladder cancer cell line BFTC905 was cultured in a 10% FBS-containing D-MEM culture medium. Upon transplantation, the cells were recovered by centrifugation, and the thus recovered cells were suspended in RPMI1640 at $5 \times 10^7$ cells/ml. This cell suspension was transplanted into the subcutis on the right abdomen of each C.B-17-scid mouse (female, 7-week-old, CLEA Japan, Inc.). After completion of the transplantation, the tumor diameter of each mouse was measured with a vernier caliper two times a week. At the time point at which the mean tumor volume reached approximately 150 $mm^3$, the mice were divided into two groups (five mice per group) according to random assignment regarding tumor volume. To one group, the PPAT-057-27C antibody was administered at an amount of 1 mg/kg into the caudal vein of each mouse. To the other group, PBS was administered at an amount of 0.2 mL/20 g mouse into the caudal vein of each mouse. Administration was carried out two times a week (every three or four days) in a total of five times. Even after completion of the administration, the tumor diameter was measured with a vernier caliper two times a week, as with before the assignment, so that the tumor volumes in each group were obtained. Antitumor effects were determined based on the mean tumor volumes on the final day of measurement according to the Student's t-test.

Tumor volume was calculated according to the following formula.

Tumor volume=(Minor axis)$^2$×Major axis×0.5

The random assignment and the Student's t-test were performed using animal experiment data statistical analysis software EXSUS (CLC Corporation).

Figure 12:
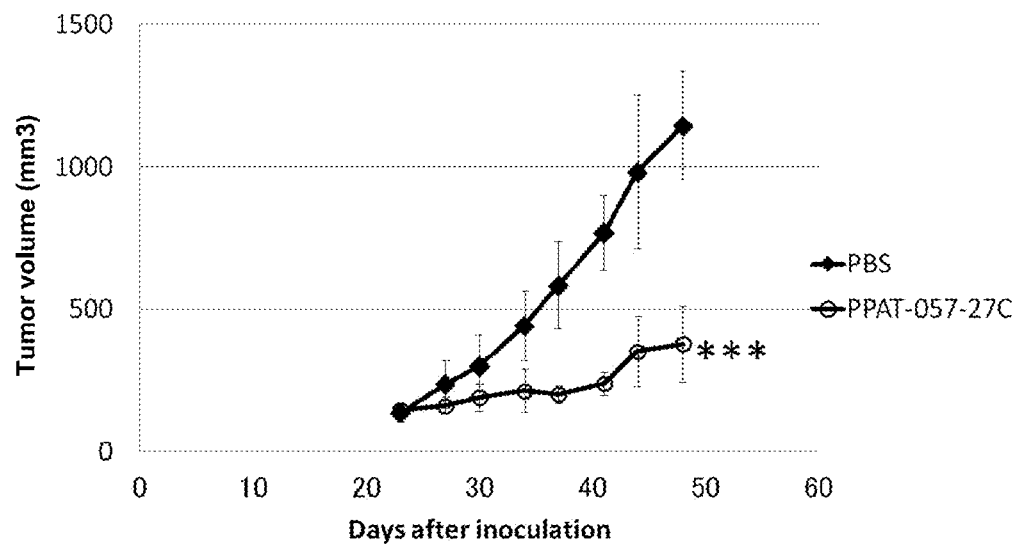
FIG. 12 shows the in vivo antitumor effects of the chimeric antibody PPAT-057-27C.

A change over time in the mean value of the tumor volumes in each group is shown in FIG. 12. As shown in FIG. 12, the growth of the tumor was suppressed by the PPAT-057-27C antibody. In the figure, the symbol *** indicates that there was a significant difference at P<0.001.

Example 12

Antitumor Effects of Chimeric Antibody PPAT-057-23C on Xenograft Models

The antitumor effects of the chimeric antibody PPAT-057-23C were confirmed using xenograft models, into which a human lung cancer-derived cell line NCI-H1650 had been transplanted.

The non-small cell lung cancer cell line NCI-H1650 was cultured in a 10% FBS-containing RPMI1640 culture medium. Upon transplantation, the cells were recovered by centrifugation, and the thus recovered cells were suspended in RPMI1640 at 5×10$^7$ cells/ml. This cell suspension was transplanted into the subcutis on the right abdomen of each C.B-17-scid mouse (female, 7-week-old, CLEA Japan, Inc.). After completion of the transplantation, the tumor diameter of each mouse was measured with a vernier caliper two times a week. At the time point at which the mean tumor volume reached approximately 150 mm$^3$, the mice were divided into two groups (six mice per group) according to random assignment regarding tumor volume. To one group, the PPAT-057-23C antibody was administered at an amount of 1.5 mg/kg into the caudal vein of each mouse. To the other group, PBS was administered as a negative control at an amount of 0.2 mL/20 g mouse into the caudal vein of each mouse. Administration was carried out once a week in a total of two times. Even after completion of the administration, the tumor diameter was measured with a vernier caliper two times a week, as with before the assignment, so that the tumor volumes in each group were obtained. Antitumor effects were determined based on the mean tumor volumes on the final day of measurement according to the Student's t-test.

Tumor volume was calculated according to the following formula.

Tumor volume=(Minor axis)$^2$×Major axis×0.5

The random assignment and the Student's t-test were performed using animal experiment data statistical analysis software EXSUS (CLC Corporation).

Figure 13:
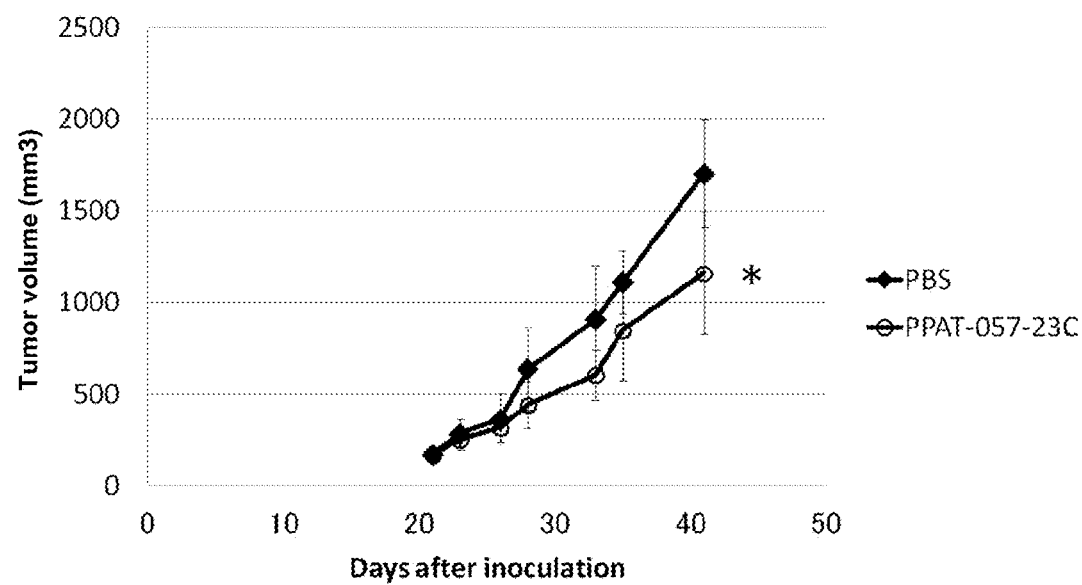
FIG. 13 shows the in vivo antitumor effects of the chimeric antibody PPAT-057-23C.

A change over time in the mean value of the tumor volumes in each group is shown in FIG. 13. As shown in FIG. 13, the growth of the tumor was suppressed by the PRAT-057-23C antibody. In the figure, the symbol * indicates that there was a significant difference at P<0.05.

The invention claimed is:

1. A recombinant antibody which specifically reacts with an epitope existing in the amino acids at positions 551 to 654 of the amino acid sequence shown in SEQ ID NO: 38 that is the extracellular region of human CDH3, and has cytotoxicity against CDH3-expressing cells, and which comprises the CDR1, CDR2 and CDR3 of a heavy chain variable region (HV), respectively, consisting of the amino acid sequences shown in SEQ ID NOS: 25-27, and the CDR1, CDR2 and CDR3 of a light chain variable region (LV), respectively, consisting of the amino acid sequences shown in SEQ ID NOS: 28-30.

2. The recombinant antibody according to claim 1, wherein the cytotoxicity is cell growth-suppressing activity or antibody-dependent cellular cytotoxicity (ADCC).

3. The recombinant antibody according to claim 1, which comprises the constant region of a human antibody.

4. The recombinant antibody according to claim 3, wherein the constant region of the human antibody consists to the constant region of a human antibody IgG1 class.

5. A cytotoxic agent comprising the recombinant antibody according to claim 1 as an active ingredient.

6. A therapeutic agent for high human CDH3 expression-related disease, which comprises the recombinant antibody according to claim 1 as an active ingredient.

7. The therapeutic agent according to claim 6, wherein the high CDH3 expression-related disease is cancer.

8. A diagnostic agent for high human CDH3 expression-related disease, which comprises the recombinant antibody according to claim 1 as an active ingredient.

9. The diagnostic agent according to claim 8, wherein the high CDH3 expression-related disease is cancer.

* * * * *

```
                        SEQUENCE LISTING

<160> NUMBER OF SEQ ID NOS: 98

<210> SEQ ID NO 1
<211> LENGTH: 6
<212> TYPE: PRT
<213> ORGANISM: mouse

<400> SEQUENCE: 1

Gln Ser Tyr Gly Val His
1               5

<210> SEQ ID NO 2
<211> LENGTH: 16
<212> TYPE: PRT
<213> ORGANISM: mouse

<400> SEQUENCE: 2

Val Ile Trp Ala Gly Gly Asn Thr Ile Tyr Asn Ser Ala Leu Met Ser
1               5                   10                  15

<210> SEQ ID NO 3
<211> LENGTH: 14
<212> TYPE: PRT
<213> ORGANISM: mouse

<400> SEQUENCE: 3

Pro His Tyr Gly Asp Tyr Ala Gly Phe Tyr Ala Leu Asp His
1               5                   10

<210> SEQ ID NO 4
<211> LENGTH: 11
<212> TYPE: PRT
```

```
<213> ORGANISM: mouse

<400> SEQUENCE: 4

Arg Ala Ser Lys Arg Ile Ser Lys Tyr Leu Ala
1               5                   10

<210> SEQ ID NO 5
<211> LENGTH: 7
<212> TYPE: PRT
<213> ORGANISM: mouse

<400> SEQUENCE: 5

Ser Gly Ser Thr Leu Gln Ser
1               5

<210> SEQ ID NO 6
<211> LENGTH: 9
<212> TYPE: PRT
<213> ORGANISM: mouse

<400> SEQUENCE: 6

Gln Gln His Asn Glu Tyr Pro Trp Thr
1               5

<210> SEQ ID NO 7
<211> LENGTH: 5
<212> TYPE: PRT
<213> ORGANISM: mouse

<400> SEQUENCE: 7

Asp Tyr Tyr Met Asp
1               5

<210> SEQ ID NO 8
<211> LENGTH: 17
<212> TYPE: PRT
<213> ORGANISM: mouse

<400> SEQUENCE: 8

Tyr Ile Tyr Pro Asn Asn Gly Gly Ala Ser Tyr Asn Gln Lys Phe Lys
1               5                   10                  15

Gly

<210> SEQ ID NO 9
<211> LENGTH: 11
<212> TYPE: PRT
<213> ORGANISM: mouse

<400> SEQUENCE: 9

Ser Arg Asp Gly Tyr Tyr Ser Gly Met Asp Tyr
1               5                   10

<210> SEQ ID NO 10
<211> LENGTH: 11
<212> TYPE: PRT
<213> ORGANISM: mouse

<400> SEQUENCE: 10

Arg Ala Ser Lys Ser Ile Asn Lys Tyr Leu Ala
1               5                   10

<210> SEQ ID NO 11
<211> LENGTH: 7
<212> TYPE: PRT
```

<213> ORGANISM: mouse

<400> SEQUENCE: 11

Ser Gly Ser Thr Leu Gln Ser
1               5

<210> SEQ ID NO 12
<211> LENGTH: 9
<212> TYPE: PRT
<213> ORGANISM: mouse

<400> SEQUENCE: 12

Gln Gln His Asn Glu Tyr Pro Leu Thr
1               5

<210> SEQ ID NO 13
<211> LENGTH: 5
<212> TYPE: PRT
<213> ORGANISM: mouse

<400> SEQUENCE: 13

Ser Tyr Val Ile His
1               5

<210> SEQ ID NO 14
<211> LENGTH: 17
<212> TYPE: PRT
<213> ORGANISM: mouse

<400> SEQUENCE: 14

Tyr Ile Asn Pro Phe Asn Asp Asn Thr Lys Tyr Asn Glu Lys Phe Lys
1               5                   10                  15

Gly

<210> SEQ ID NO 15
<211> LENGTH: 6
<212> TYPE: PRT
<213> ORGANISM: mouse

<400> SEQUENCE: 15

Arg Leu Phe Ala Asp Tyr
1               5

<210> SEQ ID NO 16
<211> LENGTH: 11
<212> TYPE: PRT
<213> ORGANISM: mouse

<400> SEQUENCE: 16

Arg Ala Ser Glu Asn Ile Asp Ser Phe Leu Ala
1               5                   10

<210> SEQ ID NO 17
<211> LENGTH: 7
<212> TYPE: PRT
<213> ORGANISM: mouse

<400> SEQUENCE: 17

Val Ala Thr Leu Leu Ala Asp
1               5

<210> SEQ ID NO 18
<211> LENGTH: 9
<212> TYPE: PRT

```
<213> ORGANISM: mouse

<400> SEQUENCE: 18

Gln His Tyr Tyr Asn Thr Pro Arg Thr
1               5

<210> SEQ ID NO 19
<211> LENGTH: 5
<212> TYPE: PRT
<213> ORGANISM: mouse

<400> SEQUENCE: 19

Gly Tyr Tyr Met His
1               5

<210> SEQ ID NO 20
<211> LENGTH: 17
<212> TYPE: PRT
<213> ORGANISM: mouse

<400> SEQUENCE: 20

Glu Ile Asn Pro Ser Thr Gly Gly Thr Thr Tyr Asn Gln Lys Phe Lys
1               5                   10                  15

Ala

<210> SEQ ID NO 21
<211> LENGTH: 9
<212> TYPE: PRT
<213> ORGANISM: mouse

<400> SEQUENCE: 21

Asp Ser Asn Tyr Val Gly Phe Ala Phe
1               5

<210> SEQ ID NO 22
<211> LENGTH: 11
<212> TYPE: PRT
<213> ORGANISM: mouse

<400> SEQUENCE: 22

Arg Ala Ser Gln Asp Ile Ser Asn Tyr Leu Asn
1               5                   10

<210> SEQ ID NO 23
<211> LENGTH: 7
<212> TYPE: PRT
<213> ORGANISM: mouse

<400> SEQUENCE: 23

Tyr Thr Ser Arg Leu His Ser
1               5

<210> SEQ ID NO 24
<211> LENGTH: 9
<212> TYPE: PRT
<213> ORGANISM: mouse

<400> SEQUENCE: 24

Gln Gln Tyr Ser Lys Phe Pro Arg Thr
1               5

<210> SEQ ID NO 25
<211> LENGTH: 5
<212> TYPE: PRT
```

```
<213> ORGANISM: mouse

<400> SEQUENCE: 25

Asp His Asn Ile Asp
1               5

<210> SEQ ID NO 26
<211> LENGTH: 17
<212> TYPE: PRT
<213> ORGANISM: mouse

<400> SEQUENCE: 26

Tyr Ile Tyr Pro Ser Asn Gly Gly Thr Gly Tyr Asn Gln Lys Phe Lys
1               5                   10                  15

Asn

<210> SEQ ID NO 27
<211> LENGTH: 13
<212> TYPE: PRT
<213> ORGANISM: mouse

<400> SEQUENCE: 27

Pro Tyr Gly Asn Asp Asp Tyr Tyr Tyr Ala Met Asp Tyr
1               5                   10

<210> SEQ ID NO 28
<211> LENGTH: 11
<212> TYPE: PRT
<213> ORGANISM: mouse

<400> SEQUENCE: 28

Arg Ala Ser Lys Ser Ile Ser Lys Tyr Leu Ala
1               5                   10

<210> SEQ ID NO 29
<211> LENGTH: 7
<212> TYPE: PRT
<213> ORGANISM: mouse

<400> SEQUENCE: 29

Ser Gly Ser Thr Leu Gln Ser
1               5

<210> SEQ ID NO 30
<211> LENGTH: 9
<212> TYPE: PRT
<213> ORGANISM: mouse

<400> SEQUENCE: 30

Gln Gln Tyr Tyr Glu Tyr Pro Tyr Thr
1               5

<210> SEQ ID NO 31
<211> LENGTH: 5
<212> TYPE: PRT
<213> ORGANISM: mouse

<400> SEQUENCE: 31

Ala Tyr Asn Met His
1               5

<210> SEQ ID NO 32
<211> LENGTH: 17
<212> TYPE: PRT
```

```
<213> ORGANISM: mouse

<400> SEQUENCE: 32

Phe Ile Asp Pro Tyr Ser Gly Ile Ile Thr Tyr Asn Gln Thr Phe Lys
 1               5                  10                  15

Gly

<210> SEQ ID NO 33
<211> LENGTH: 10
<212> TYPE: PRT
<213> ORGANISM: mouse

<400> SEQUENCE: 33

Arg Gly Tyr Tyr Asp Gly Gly Phe Asp Tyr
 1               5                  10

<210> SEQ ID NO 34
<211> LENGTH: 11
<212> TYPE: PRT
<213> ORGANISM: mouse

<400> SEQUENCE: 34

Arg Ala Ser Gln Asp Ile Thr Asn Tyr Leu Asn
 1               5                  10

<210> SEQ ID NO 35
<211> LENGTH: 7
<212> TYPE: PRT
<213> ORGANISM: mouse

<400> SEQUENCE: 35

Tyr Thr Ser Arg Leu His Ser
 1               5

<210> SEQ ID NO 36
<211> LENGTH: 9
<212> TYPE: PRT
<213> ORGANISM: mouse

<400> SEQUENCE: 36

Gln Gln Asp Ser Lys His Pro Arg Thr
 1               5

<210> SEQ ID NO 37
<211> LENGTH: 2490
<212> TYPE: DNA
<213> ORGANISM: human
<220> FEATURE:
<221> NAME/KEY: CDS
<222> LOCATION: (1)..(2490)

<400> SEQUENCE: 37 atg ggg ctc cct cgt gga cct ctc gcg tct ctc ctc ctt ctc cag gtt     48
Met Gly Leu Pro Arg Gly Pro Leu Ala Ser Leu Leu Leu Leu Gln Val
 1               5                  10                  15 tgc tgg ctg cag tgc gcg gcc tcc gag ccg tgc cgg gcg gtc ttc agg     96
Cys Trp Leu Gln Cys Ala Ala Ser Glu Pro Cys Arg Ala Val Phe Arg
                20                  25                  30 gag gct gaa gtg acc ttg gag gcg gga ggc gcg gag cag gag ccc ggc    144
Glu Ala Glu Val Thr Leu Glu Ala Gly Gly Ala Glu Gln Glu Pro Gly
            35                  40                  45 cag gcg ctg ggg aaa gta ttc atg ggc tgc cct ggg caa gag cca gct    192
Gln Ala Leu Gly Lys Val Phe Met Gly Cys Pro Gly Gln Glu Pro Ala
        50                  55                  60
```

|  |  |
|---|---:|
| ctg ttt agc act gat aat gat gac ttc act gtg cgg aat ggc gag aca<br>Leu Phe Ser Thr Asp Asn Asp Asp Phe Thr Val Arg Asn Gly Glu Thr<br>65                       70                     75                 80 | 240 |
| gtc cag gaa aga agg tca ctg aag gaa agg aat cca ttg aag atc ttc<br>Val Gln Glu Arg Arg Ser Leu Lys Glu Arg Asn Pro Leu Lys Ile Phe<br>                     85                     90                     95 | 288 |
| cca tcc aaa cgt atc tta cga aga cac aag aga gat tgg gtg gtt gct<br>Pro Ser Lys Arg Ile Leu Arg Arg His Lys Arg Asp Trp Val Val Ala<br>                100                    105                  110 | 336 |
| cca ata tct gtc cct gaa aat ggc aag ggt ccc ttc ccc cag aga ctg<br>Pro Ile Ser Val Pro Glu Asn Gly Lys Gly Pro Phe Pro Gln Arg Leu<br>             115                    120                  125 | 384 |
| aat cag ctc aag tct aat aaa gat aga gac acc aag att ttc tac agc<br>Asn Gln Leu Lys Ser Asn Lys Asp Arg Asp Thr Lys Ile Phe Tyr Ser<br>130                      135                  140 | 432 |
| atc acg ggg ccg ggg gca gac agc ccc cct gag ggt gtc ttc gct gta<br>Ile Thr Gly Pro Gly Ala Asp Ser Pro Pro Glu Gly Val Phe Ala Val<br>145                      150                  155                  160 | 480 |
| gag aag gag aca ggc tgg ttg ttg ttg aat aag cca ctg gac cgg gag<br>Glu Lys Glu Thr Gly Trp Leu Leu Leu Asn Lys Pro Leu Asp Arg Glu<br>                             165                  170                  175 | 528 |
| gag att gcc aag tat gag ctc ttt ggc cac gct gtg tca gag aat ggt<br>Glu Ile Ala Lys Tyr Glu Leu Phe Gly His Ala Val Ser Glu Asn Gly<br>                    180                    185                  190 | 576 |
| gcc tca gtg gag gac ccc atg aac atc tcc atc atc gtg acc gac cag<br>Ala Ser Val Glu Asp Pro Met Asn Ile Ser Ile Ile Val Thr Asp Gln<br>             195                    200                  205 | 624 |
| aat gac cac aag ccc aag ttt acc cag gac acc ttc cga ggg agt gtc<br>Asn Asp His Lys Pro Lys Phe Thr Gln Asp Thr Phe Arg Gly Ser Val<br>210                      215                  220 | 672 |
| tta gag gga gtc cta cca ggt act tct gtg atg cag gtg aca gcc acg<br>Leu Glu Gly Val Leu Pro Gly Thr Ser Val Met Gln Val Thr Ala Thr<br>225                      230                  235                  240 | 720 |
| gat gag gat gat gcc atc tac acc tac aat ggg gtg gtt gct tac tcc<br>Asp Glu Asp Asp Ala Ile Tyr Thr Tyr Asn Gly Val Val Ala Tyr Ser<br>                             245                  250                  255 | 768 |
| atc cat agc caa gaa cca aag gac cca cac gac ctc atg ttc acc att<br>Ile His Ser Gln Glu Pro Lys Asp Pro His Asp Leu Met Phe Thr Ile<br>             260                    265                  270 | 816 |
| cac cgg agc aca ggc acc atc agc gtc atc tcc agt ggc ctg gac cgg<br>His Arg Ser Thr Gly Thr Ile Ser Val Ile Ser Ser Gly Leu Asp Arg<br>                    275                    280                  285 | 864 |
| gaa aaa gtc cct gag tac aca ctg acc atc cag gcc aca gac atg gat<br>Glu Lys Val Pro Glu Tyr Thr Leu Thr Ile Gln Ala Thr Asp Met Asp<br>290                      295                  300 | 912 |
| ggg gac ggc tcc acc acc acg gca gtg gca gta gtg gag atc ctt gat<br>Gly Asp Gly Ser Thr Thr Thr Ala Val Ala Val Val Glu Ile Leu Asp<br>305                      310                  315                  320 | 960 |
| gcc aat gac aat gct ccc atg ttt gac ccc cag aag tac gag gcc cat<br>Ala Asn Asp Asn Ala Pro Met Phe Asp Pro Gln Lys Tyr Glu Ala His<br>                         325                    330                  335 | 1008 |
| gtg cct gag aat gca gtg ggc cat gag gtg cag agg ctg acg gtc act<br>Val Pro Glu Asn Ala Val Gly His Glu Val Gln Arg Leu Thr Val Thr<br>                    340                    345                  350 | 1056 |
| gat ctg gac gcc ccc aac tca cca gcg tgg cgt gcc acc tac ctt atc<br>Asp Leu Asp Ala Pro Asn Ser Pro Ala Trp Arg Ala Thr Tyr Leu Ile<br>             355                    360                  365 | 1104 |
| atg ggc ggt gac gac ggg gac cat ttt acc atc acc acc cac cct gag<br>Met Gly Gly Asp Asp Gly Asp His Phe Thr Ile Thr Thr His Pro Glu | 1152 |

|  |  |
|---|---|
| agc aac cag ggc atc ctg aca acc agg aag ggt ttg gat ttt gag gcc<br>Ser Asn Gln Gly Ile Leu Thr Thr Arg Lys Gly Leu Asp Phe Glu Ala<br>385      390      395      400 | 1200 |
| aaa aac cag cac acc ctg tac gtt gaa gtg acc aac gag gcc cct ttt<br>Lys Asn Gln His Thr Leu Tyr Val Glu Val Thr Asn Glu Ala Pro Phe<br>      405      410      415 | 1248 |
| gtg ctg aag ctc cca acc tcc aca gcc acc ata gtg gtc cac gtg gag<br>Val Leu Lys Leu Pro Thr Ser Thr Ala Thr Ile Val Val His Val Glu<br>  420      425      430 | 1296 |
| gat gtg aat gag gca cct gtg ttt gtc cca ccc tcc aaa gtc gtt gag<br>Asp Val Asn Glu Ala Pro Val Phe Val Pro Pro Ser Lys Val Val Glu<br>  435      440      445 | 1344 |
| gtc cag gag ggc atc ccc act ggg gag cct gtg tgt gtc tac act gca<br>Val Gln Glu Gly Ile Pro Thr Gly Glu Pro Val Cys Val Tyr Thr Ala<br>450      455      460 | 1392 |
| gaa gac cct gac aag gag aat caa aag atc agc tac cgc atc ctg aga<br>Glu Asp Pro Asp Lys Glu Asn Gln Lys Ile Ser Tyr Arg Ile Leu Arg<br>465      470      475      480 | 1440 |
| gac cca gca ggg tgg cta gcc atg gac cca gac agt ggg cag gtc aca<br>Asp Pro Ala Gly Trp Leu Ala Met Asp Pro Asp Ser Gly Gln Val Thr<br>      485      490      495 | 1488 |
| gct gtg ggc acc ctc gac cgt gag gat gag cag ttt gtg agg aac aac<br>Ala Val Gly Thr Leu Asp Arg Glu Asp Glu Gln Phe Val Arg Asn Asn<br>  500      505      510 | 1536 |
| atc tat gaa gtc atg gtc ttg gcc atg gac aat gga agc cct ccc acc<br>Ile Tyr Glu Val Met Val Leu Ala Met Asp Asn Gly Ser Pro Pro Thr<br>  515      520      525 | 1584 |
| act ggc acg gga acc ctt ctg cta aca ctg att gat gtc aat gac cat<br>Thr Gly Thr Gly Thr Leu Leu Leu Thr Leu Ile Asp Val Asn Asp His<br>530      535      540 | 1632 |
| ggc cca gtc cct gag ccc cgt cag atc acc atc tgc aac caa agc cct<br>Gly Pro Val Pro Glu Pro Arg Gln Ile Thr Ile Cys Asn Gln Ser Pro<br>545      550      555      560 | 1680 |
| gtg cgc cag gtg ctg aac atc acg gac aag gac ctg tct ccc cac acc<br>Val Arg Gln Val Leu Asn Ile Thr Asp Lys Asp Leu Ser Pro His Thr<br>      565      570      575 | 1728 |
| tcc cct ttc cag gcc cag ctc aca gat gac tca gac atc tac tgg acg<br>Ser Pro Phe Gln Ala Gln Leu Thr Asp Asp Ser Asp Ile Tyr Trp Thr<br>      580      585      590 | 1776 |
| gca gag gtc aac gag gaa ggt gac aca gtg gtc ttg tcc ctg aag aag<br>Ala Glu Val Asn Glu Glu Gly Asp Thr Val Val Leu Ser Leu Lys Lys<br>      595      600      605 | 1824 |
| ttc ctg aag cag gat aca tat gac gtg cac ctt tct ctg tct gac cat<br>Phe Leu Lys Gln Asp Thr Tyr Asp Val His Leu Ser Leu Ser Asp His<br>610      615      620 | 1872 |
| ggc aac aaa gag cag ctg acg gtg atc agg gcc act gtg tgc gac tgc<br>Gly Asn Lys Glu Gln Leu Thr Val Ile Arg Ala Thr Val Cys Asp Cys<br>625      630      635      640 | 1920 |
| cat ggc cat gtc gaa acc tgc cct gga ccc tgg aag gga ggt ttc atc<br>His Gly His Val Glu Thr Cys Pro Gly Pro Trp Lys Gly Gly Phe Ile<br>      645      650      655 | 1968 |
| ctc cct gtg ctg ggg gct gtc ctg gct ctg ctg ttc ctc ctg ctg gtg<br>Leu Pro Val Leu Gly Ala Val Leu Ala Leu Leu Phe Leu Leu Leu Val<br>  660      665      670 | 2016 |
| ctg ctt ttg ttg gtg aga aag aag cgg aag atc aag gag ccc ctc cta<br>Leu Leu Leu Leu Val Arg Lys Lys Arg Lys Ile Lys Glu Pro Leu Leu<br>  675      680      685 | 2064 |
| ctc cca gaa gat gac acc cgt gac aac gtc ttc tac tat ggc gaa gag | 2112 |

```
                                                    -continued

Leu Pro Glu Asp Asp Thr Arg Asp Asn Val Phe Tyr Tyr Gly Glu Glu
    690                 695                 700 ggg ggt ggc gaa gag gac cag gac tat gac atc acc cag ctc cac cga    2160
Gly Gly Gly Glu Glu Asp Gln Asp Tyr Asp Ile Thr Gln Leu His Arg
705                 710                 715                 720 ggt ctg gag gcc agg ccg gag gtg gtt ctc cgc aat gac gtg gca cca    2208
Gly Leu Glu Ala Arg Pro Glu Val Val Leu Arg Asn Asp Val Ala Pro
                725                 730                 735 acc atc atc ccg aca ccc atg tac cgt cct cgg cca gcc aac cca gat    2256
Thr Ile Ile Pro Thr Pro Met Tyr Arg Pro Arg Pro Ala Asn Pro Asp
            740                 745                 750 gaa atc ggc aac ttt ata att gag aac ctg aag gcg gct aac aca gac    2304
Glu Ile Gly Asn Phe Ile Ile Glu Asn Leu Lys Ala Ala Asn Thr Asp
        755                 760                 765 ccc aca gcc ccg ccc tac gac acc ctc ttg gtg ttc gac tat gag ggc    2352
Pro Thr Ala Pro Pro Tyr Asp Thr Leu Leu Val Phe Asp Tyr Glu Gly
    770                 775                 780 agc ggc tcc gac gcc gcg tcc ctg agc tcc ctc acc tcc tcc gcc tcc    2400
Ser Gly Ser Asp Ala Ala Ser Leu Ser Ser Leu Thr Ser Ser Ala Ser
785                 790                 795                 800 gac caa gac caa gat tac gat tat ctg aac gag tgg ggc agc cgc ttc    2448
Asp Gln Asp Gln Asp Tyr Asp Tyr Leu Asn Glu Trp Gly Ser Arg Phe
                805                 810                 815 aag aag ctg gca gac atg tac ggt ggc ggg gag gac gac tag            2490
Lys Lys Leu Ala Asp Met Tyr Gly Gly Gly Glu Asp Asp
            820                 825

<210> SEQ ID NO 38
<211> LENGTH: 829
<212> TYPE: PRT
<213> ORGANISM: human

<400> SEQUENCE: 38

Met Gly Leu Pro Arg Gly Pro Leu Ala Ser Leu Leu Leu Leu Gln Val
1               5                   10                  15

Cys Trp Leu Gln Cys Ala Ala Ser Glu Pro Cys Arg Ala Val Phe Arg
            20                  25                  30

Glu Ala Glu Val Thr Leu Glu Ala Gly Gly Ala Glu Gln Glu Pro Gly
        35                  40                  45

Gln Ala Leu Gly Lys Val Phe Met Gly Cys Pro Gly Gln Glu Pro Ala
    50                  55                  60

Leu Phe Ser Thr Asp Asn Asp Asp Phe Thr Val Arg Asn Gly Glu Thr
65                  70                  75                  80

Val Gln Glu Arg Arg Ser Leu Lys Glu Arg Asn Pro Leu Lys Ile Phe
                85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
        115                 120                 125

Asn Gln Leu Lys Ser Asn Lys Asp Arg Asp Thr Lys Ile Phe Tyr Ser
    130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190
```

-continued

```
Ala Ser Val Glu Asp Pro Met Asn Ile Ser Ile Val Thr Asp Gln
        195                 200                 205

Asn Asp His Lys Pro Lys Phe Thr Gln Asp Thr Phe Arg Gly Ser Val
210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile
                260                 265                 270

His Arg Ser Thr Gly Thr Ile Ser Val Ile Ser Ser Gly Leu Asp Arg
        275                 280                 285

Glu Lys Val Pro Glu Tyr Thr Leu Thr Ile Gln Ala Thr Asp Met Asp
        290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
                340                 345                 350

Asp Leu Asp Ala Pro Asn Ser Pro Ala Trp Arg Ala Thr Tyr Leu Ile
        355                 360                 365

Met Gly Gly Asp Asp Gly Asp His Phe Thr Ile Thr Thr His Pro Glu
        370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
                405                 410                 415

Val Leu Lys Leu Pro Thr Ser Thr Ala Thr Ile Val Val His Val Glu
                420                 425                 430

Asp Val Asn Glu Ala Pro Val Phe Val Pro Pro Ser Lys Val Val Glu
        435                 440                 445

Val Gln Glu Gly Ile Pro Thr Gly Glu Pro Val Cys Val Tyr Thr Ala
        450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
                485                 490                 495

Ala Val Gly Thr Leu Asp Arg Glu Asp Glu Gln Phe Val Arg Asn Asn
                500                 505                 510

Ile Tyr Glu Val Met Val Leu Ala Met Asp Asn Gly Ser Pro Pro Thr
        515                 520                 525

Thr Gly Thr Gly Thr Leu Leu Leu Thr Leu Ile Asp Val Asn Asp His
        530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
                565                 570                 575

Ser Pro Phe Gln Ala Gln Leu Thr Asp Ser Asp Ile Tyr Trp Thr
                580                 585                 590

Ala Glu Val Asn Glu Glu Gly Asp Thr Val Val Leu Ser Leu Lys Lys
        595                 600                 605

Phe Leu Lys Gln Asp Thr Tyr Asp Val His Leu Ser Leu Ser Asp His
```

```
                610             615             620
Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly Phe Ile
                645                 650                 655

Leu Pro Val Leu Gly Ala Val Leu Ala Leu Phe Leu Leu Leu Leu Val
            660                 665                 670

Leu Leu Leu Leu Val Arg Lys Lys Arg Lys Ile Lys Glu Pro Leu Leu
        675                 680                 685

Leu Pro Glu Asp Asp Thr Arg Asp Asn Val Phe Tyr Tyr Gly Glu Glu
    690                 695                 700

Gly Gly Gly Glu Glu Asp Gln Asp Tyr Asp Ile Thr Gln Leu His Arg
705                 710                 715                 720

Gly Leu Glu Ala Arg Pro Glu Val Val Leu Arg Asn Asp Val Ala Pro
                725                 730                 735

Thr Ile Ile Pro Thr Pro Met Tyr Arg Pro Arg Pro Ala Asn Pro Asp
                740                 745                 750

Glu Ile Gly Asn Phe Ile Ile Glu Asn Leu Lys Ala Ala Asn Thr Asp
            755                 760                 765

Pro Thr Ala Pro Pro Tyr Asp Thr Leu Leu Val Phe Asp Tyr Glu Gly
        770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                805                 810                 815

Lys Lys Leu Ala Asp Met Tyr Gly Gly Gly Glu Asp Asp
                820                 825

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
cgcggtacca tggggctccc tcgt                                           24

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
ccgtctagat aacctcccttt ccagggtcc                                     29

<210> SEQ ID NO 41
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
tatggagctc ggtaccgatt gggtggttgc tccaatatct g                        41
```

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
agattaccta tctagactac tgcatcacag aagtacctgg tagg            44

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
tatggagctc ggtaccaagt ctaataaaga tagagacacc aag             43

<210> SEQ ID NO 44
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
agattaccta tctagactac ctctgcacct catggcccac tgcattctca      50

<210> SEQ ID NO 45
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
tatggagctc ggtaccgtga cagccacgga tgaggatgat g               41

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
agattaccta tctagactag acacacacag gctccccagt g               41

<210> SEQ ID NO 47
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 47
tatggagctc ggtaccctga cggtcactga tctggacg                   38

<210> SEQ ID NO 48
<211> LENGTH: 47
<212> TYPE: DNA
<213> ORGANISM: Artificial Sequence
<220> FEATURE:
<223> OTHER INFORMATION: Description of Artificial Sequence: Synthetic DNA

<400> SEQUENCE: 48
agattaccta tctagactag ggctcaggga ctgggccatg gtcattg    47

<210> SEQ ID NO 49
<211> LENGTH: 41
<212> TYPE: DNA
<213> ORGANISM: Artificial Sequence
<220> FEATURE:
<223> OTHER INFORMATION: Description of Artificial Sequence: Synthetic DNA

<400> SEQUENCE: 49
tatggagctc ggtacctaca ctgcagaaga ccctgacaag g    41

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence: Synthetic DNA

<400> SEQUENCE: 50
agattaccta tctagactaa cctcccttcc agggtccagg gcaggtttcg    50

<210> SEQ ID NO 51
<211> LENGTH: 107
<212> TYPE: PRT
<213> ORGANISM: mouse

<400> SEQUENCE: 51

Asp Val Gln Ile Thr Gln Ser Pro Ser Tyr Leu Ala Ala Ser Pro Gly
1               5                   10                  15

Glu Thr Ile Asn Ile Asn Cys Arg Ala Ser Lys Arg Ile Ser Lys Tyr
            20                  25                  30

Leu Ala Trp Tyr Gln Glu Lys Pro Gly Lys Thr Asn Arg Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys
            100                 105

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 52
gayatccagc tgactcagcc                                                  20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 53
gayattgttc tcwcccagtc                                                  20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 54
gayattgtgm tmactcagtc                                                  20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 55
gayattgtgy tracacagtc                                                  20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 56
gayattgtra tgacmcagtc                                                  20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 57
gayattmaga tramccagtc                                                  20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 58
gayattcaga tgaydcagtc                                                  20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 59
gayatycaga tgacacagac                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 60
gayattgttc tcawccagtc                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 61
gayattgwgc tsacccaatc                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 62
gayattstra tgaccccartc                                             20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 63
gayrttktga tgacccarac                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 64
gayattgtga tgacbcagkc                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 65
gayattgtga taacycagga                                               20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 66
gayattgtga tgacccagwt                                               20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 67
gayattgtga tgacacaacc                                               20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 68
gayattttgc tgactcagtc                                               20

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic DNA

<400> SEQUENCE: 69
ggsaccaarc tggaaatmaa a                                             21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic DNA

<400> SEQUENCE: 70
gggacaaagt tggaaataaa a                                             21

```
<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 71
gggaccaagc tggagctgaa a                                              21

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 72
atgragwcac akwcycaggt cttt                                           24

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 73
atggagacag acacactcct gctat                                          25

<210> SEQ ID NO 74
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 74
atggagwcag acacactsct gytatgggt                                      29

<210> SEQ ID NO 75
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: misc_feature
<222> LOCATION: (27)..(27)
<223> OTHER INFORMATION: n is inosine

<400> SEQUENCE: 75
atgaggrccc ctgctcagwt tyttggnwtc tt                                  32

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 76
```
atgggcwtca agatgragtc acakwyycwg g         31

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 77
atgagtgtgc ycactcaggt cctggsgtt         29

<210> SEQ ID NO 78
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 78
atgtggggay cgktttyamm cttttcaatt g         31

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 79
atggaagccc cagctcagct tctcttcc         28

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: misc_feature
<222> LOCATION: (1)..(26)
<223> OTHER INFORMATION: any n is inosine

<400> SEQUENCE: 80
atgagnmmkt cnmttcantt cytggg         26

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: misc_feature
<222> LOCATION: (1)..(26)
<223> OTHER INFORMATION: any n is inosine

<400> SEQUENCE: 81
atgakgthcy cngctcagyt yctnrg         26

<210> SEQ ID NO 82
<211> LENGTH: 25
<212> TYPE: DNA

```
<213> ORGANISM: Artificial Sequence
<220> FEATURE:
<223> OTHER INFORMATION: Description of Artificial Sequence: Synthetic
      DNA

<400> SEQUENCE: 82
atggtrtccw casctcagtt ccttg                                              25

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 83
atgtatatat gtttgttgtc tatttct                                            27

<210> SEQ ID NO 84
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 84
atgaagttgc ctgttaggct gttggtgct                                          29

<210> SEQ ID NO 85
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 85
atggatttwc argtgcagat twtcagctt                                          29

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 86
atggtyctya tvtccttgct gttctgg                                            27

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 87
atggtyctya tvttrctgct gctatgg                                            27

<210> SEQ ID NO 88
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      DNA

<400> SEQUENCE: 88
actggatggt gggaagatgg a                                           21

<210> SEQ ID NO 89
<211> LENGTH: 122
<212> TYPE: PRT
<213> ORGANISM: mouse

<400> SEQUENCE: 89

Gln Val Lys Leu Glu Glu Ser Gly Pro Val Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Ile Arg His Pro Pro Gly Lys Gly Leu Glu Trp Leu
        35                  40                  45

Gly Val Ile Trp Ala Gly Gly Asn Thr Ile Tyr Asn Ser Ala Leu Met
    50                  55                  60

Ser Arg Leu Asn Ile Ser Lys Asp Asn Ser Lys Ser Gln Val Phe Leu
65                  70                  75                  80

Lys Met Asn Ser Leu Gln Ser Asp Asp Ser Ala Met Tyr Tyr Cys Ala
                85                  90                  95

Lys Pro His Tyr Gly Asp Tyr Ala Gly Phe Tyr Ala Leu Asp His Trp
            100                 105                 110

Gly Gln Gly Thr Ser Val Thr Val Ser Ser
        115                 120

<210> SEQ ID NO 90
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 90
atggratgsa gctgkgtmat sctctt                                      26

<210> SEQ ID NO 91
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 91
atgracttcg ggytgagctk ggtttt                                      26

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 92
atggctgtct tggggctgct cttct                                       25
```

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 93
atggrcagrc ttacwtyy                                                   18

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 94
saggtsmarc tksagsagtc wgg                                             23

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 95 cascccatc dgtctatcc                                                   19

<210> SEQ ID NO 96
<211> LENGTH: 728
<212> TYPE: PRT
<213> ORGANISM: Homo sapiens
<220> FEATURE:
<221> NAME/KEY: misc_feature
<223> OTHER INFORMATION: E-CADHERIN

<400> SEQUENCE: 96

Asp Trp Val Ile Pro Pro Ile Ser Cys Pro Glu Asn Glu Lys Gly Pro
1               5                   10                  15

Phe Pro Lys Asn Leu Val Gln Ile Lys Ser Asn Lys Asp Lys Glu Gly
            20                  25                  30

Lys Val Phe Tyr Ser Ile Thr Gly Gln Gly Ala Asp Thr Pro Pro Val
        35                  40                  45

Gly Val Phe Ile Ile Glu Arg Glu Thr Gly Trp Leu Lys Val Thr Glu
    50                  55                  60

Pro Leu Asp Arg Glu Arg Ile Ala Thr Tyr Thr Leu Phe Ser His Ala
65                  70                  75                  80

Val Ser Ser Asn Gly Asn Ala Val Glu Asp Pro Met Glu Ile Leu Ile
                85                  90                  95

Thr Val Thr Asp Gln Asn Asp Asn Lys Pro Glu Phe Thr Gln Glu Val
            100                 105                 110

Phe Lys Gly Ser Val Met Glu Gly Ala Leu Pro Gly Thr Ser Val Met
        115                 120                 125

Glu Val Thr Ala Thr Asp Ala Asp Asp Val Asn Thr Tyr Asn Ala
    130                 135                 140

Ala Ile Ala Tyr Thr Ile Leu Ser Gln Asp Pro Glu Leu Pro Asp Lys
145                 150                 155                 160

-continued

Asn Met Phe Thr Ile Asn Arg Asn Thr Gly Val Ile Ser Val Val Thr
                165                 170                 175

Thr Gly Leu Asp Arg Glu Ser Phe Pro Thr Tyr Thr Leu Val Val Gln
                180                 185                 190

Ala Ala Asp Leu Gln Gly Glu Gly Leu Ser Thr Thr Ala Thr Ala Val
                195                 200                 205

Ile Thr Val Thr Asp Thr Asn Asp Asn Pro Pro Ile Phe Asn Pro Thr
        210                 215                 220

Thr Tyr Lys Gly Gln Val Pro Glu Asn Glu Ala Asn Val Val Ile Thr
225                 230                 235                 240

Thr Leu Lys Val Thr Asp Ala Asp Ala Pro Asn Thr Pro Ala Trp Glu
                245                 250                 255

Ala Val Tyr Thr Ile Leu Asn Asp Asp Gly Gly Gln Phe Val Val Thr
                260                 265                 270

Thr Asn Pro Val Asn Asn Asp Gly Ile Leu Lys Thr Ala Lys Gly Leu
                275                 280                 285

Asp Phe Glu Ala Lys Gln Gln Tyr Ile Leu His Val Ala Val Thr Asn
        290                 295                 300

Val Val Pro Phe Glu Val Ser Leu Thr Thr Ser Thr Ala Thr Val Thr
305                 310                 315                 320

Val Asp Val Leu Asp Val Asn Glu Ala Pro Ile Phe Val Pro Pro Glu
                325                 330                 335

Lys Arg Val Glu Val Ser Glu Asp Phe Gly Val Gly Gln Glu Ile Thr
                340                 345                 350

Ser Tyr Thr Ala Gln Glu Pro Asp Thr Phe Met Glu Gln Lys Ile Thr
                355                 360                 365

Tyr Arg Ile Trp Arg Asp Thr Ala Asn Trp Leu Glu Ile Asn Pro Asp
        370                 375                 380

Thr Gly Ala Ile Ser Thr Arg Ala Glu Leu Asp Arg Glu Asp Phe Glu
385                 390                 395                 400

His Val Lys Asn Ser Thr Tyr Thr Ala Leu Ile Ile Ala Thr Asp Asn
                405                 410                 415

Gly Ser Pro Val Ala Thr Gly Thr Gly Thr Leu Leu Leu Ile Leu Ser
                420                 425                 430

Asp Val Asn Asp Asn Ala Pro Ile Pro Glu Pro Arg Thr Ile Phe Phe
        435                 440                 445

Cys Glu Arg Asn Pro Lys Pro Gln Val Ile Asn Ile Ile Asp Ala Asp
450                 455                 460

Leu Pro Pro Asn Thr Ser Pro Phe Thr Ala Glu Leu Thr His Gly Ala
465                 470                 475                 480

Ser Ala Asn Trp Thr Ile Gln Tyr Asn Asp Pro Thr Gln Glu Ser Ile
                485                 490                 495

Ile Leu Lys Pro Lys Met Ala Leu Glu Val Gly Asp Tyr Lys Ile Asn
                500                 505                 510

Leu Lys Leu Met Asp Asn Gln Asn Lys Asp Gln Val Thr Thr Leu Glu
        515                 520                 525

Val Ser Val Cys Asp Cys Glu Gly Ala Ala Gly Val Cys Arg Lys Ala
530                 535                 540

Gln Pro Val Glu Ala Gly Leu Gln Ile Pro Ala Ile Leu Gly Ile Leu
545                 550                 555                 560

Gly Gly Ile Leu Ala Leu Leu Ile Leu Ile Leu Leu Leu Leu Leu Phe
                565                 570                 575

```
Leu Arg Arg Arg Ala Val Val Lys Glu Pro Leu Leu Pro Pro Glu Asp
                580                 585                 590

Asp Thr Arg Asp Asn Val Tyr Tyr Asp Glu Glu Gly Gly Gly Glu
            595                 600                 605

Glu Asp Gln Asp Phe Asp Leu Ser Gln Leu His Arg Gly Leu Asp Ala
    610                 615                 620

Arg Pro Glu Val Thr Arg Asn Asp Val Ala Pro Thr Leu Met Ser Val
625                 630                 635                 640

Pro Arg Tyr Leu Pro Arg Pro Ala Asn Pro Asp Glu Ile Gly Asn Phe
                645                 650                 655

Ile Asp Glu Asn Leu Lys Ala Ala Asp Thr Asp Pro Thr Ala Pro Pro
            660                 665                 670

Tyr Asp Ser Leu Leu Val Phe Asp Tyr Glu Gly Ser Gly Ser Glu Ala
                675                 680                 685

Ala Ser Leu Ser Ser Leu Asn Ser Ser Glu Ser Asp Lys Asp Gln Asp
        690                 695                 700

Tyr Asp Tyr Leu Asn Glu Trp Gly Asn Arg Phe Lys Lys Leu Ala Asp
705                 710                 715                 720

Met Tyr Gly Gly Gly Glu Asp Asp
                725

<210> SEQ ID NO 97
<211> LENGTH: 747
<212> TYPE: PRT
<213> ORGANISM: Homo sapiens
<220> FEATURE:
<221> NAME/KEY: misc_feature
<223> OTHER INFORMATION: N-CADHERIN

<400> SEQUENCE: 97

Asp Trp Val Ile Pro Pro Ile Asn Leu Pro Glu Asn Ser Arg Gly Pro
1               5                   10                  15

Phe Pro Gln Glu Leu Val Arg Ile Arg Ser Asp Arg Asp Lys Asn Leu
            20                  25                  30

Ser Leu Arg Tyr Ser Val Thr Gly Pro Gly Ala Asp Gln Pro Pro Thr
        35                  40                  45

Gly Ile Phe Ile Leu Asn Pro Ile Ser Gly Gln Leu Ser Val Thr Lys
    50                  55                  60

Pro Leu Asp Arg Glu Gln Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe Leu His Gln Val
            100                 105                 110

Trp Asn Gly Thr Val Pro Glu Gly Ser Lys Pro Gly Thr Tyr Val Met
        115                 120                 125

Thr Val Thr Ala Ile Asp Ala Asp Asp Pro Asn Ala Leu Asn Gly Met
    130                 135                 140

Leu Arg Tyr Arg Ile Val Ser Gln Ala Pro Ser Thr Pro Ser Pro Asn
145                 150                 155                 160

Met Phe Thr Ile Asn Asn Glu Thr Gly Asp Ile Ile Thr Val Ala Ala
                165                 170                 175

Gly Leu Asp Arg Glu Lys Val Gln Gln Tyr Thr Leu Ile Ile Gln Ala
            180                 185                 190

Thr Asp Met Glu Gly Asn Pro Thr Tyr Gly Leu Ser Asn Thr Ala Thr
        195                 200                 205
```

-continued

Ala Val Ile Thr Val Thr Asp Val Asn Asp Asn Pro Pro Glu Phe Thr
    210                 215                 220

Ala Met Thr Phe Tyr Gly Glu Val Pro Glu Asn Arg Val Asp Ile Ile
225                 230                 235                 240

Val Ala Asn Leu Thr Val Thr Asp Lys Asp Gln Pro His Thr Pro Ala
                245                 250                 255

Trp Asn Ala Val Tyr Arg Ile Ser Gly Gly Asp Pro Thr Gly Arg Phe
                260                 265                 270

Ala Ile Gln Thr Asp Pro Asn Ser Asn Asp Gly Leu Val Thr Val Val
            275                 280                 285

Lys Pro Ile Asp Phe Glu Thr Asn Arg Met Phe Val Leu Thr Val Ala
290                 295                 300

Ala Glu Asn Gln Val Pro Leu Ala Lys Gly Ile Gln His Pro Pro Gln
305                 310                 315                 320

Ser Thr Ala Thr Val Ser Val Thr Val Ile Asp Val Asn Glu Asn Pro
                325                 330                 335

Tyr Phe Ala Pro Asn Pro Lys Ile Ile Arg Gln Glu Glu Gly Leu His
                340                 345                 350

Ala Gly Thr Met Leu Thr Thr Phe Thr Ala Gln Asp Pro Asp Arg Tyr
            355                 360                 365

Met Gln Gln Asn Ile Arg Tyr Thr Lys Leu Ser Asp Pro Ala Asn Trp
370                 375                 380

Leu Lys Ile Asp Pro Val Asn Gly Gln Ile Thr Thr Ile Ala Val Leu
385                 390                 395                 400

Asp Arg Glu Ser Pro Asn Val Lys Asn Asn Ile Tyr Asn Ala Thr Phe
                405                 410                 415

Leu Ala Ser Asp Asn Gly Ile Pro Pro Met Ser Gly Thr Gly Thr Leu
                420                 425                 430

Gln Ile Tyr Leu Leu Asp Ile Asn Asp Asn Ala Pro Gln Val Leu Pro
            435                 440                 445

Gln Glu Ala Glu Thr Cys Glu Thr Pro Asp Pro Asn Ser Ile Asn Ile
450                 455                 460

Thr Ala Leu Asp Tyr Asp Ile Asp Pro Asn Ala Gly Pro Phe Ala Phe
465                 470                 475                 480

Asp Leu Pro Leu Ser Pro Val Thr Ile Lys Arg Asn Trp Thr Ile Thr
                485                 490                 495

Arg Leu Asn Gly Asp Phe Ala Gln Leu Asn Leu Lys Ile Lys Phe Leu
                500                 505                 510

Glu Ala Gly Ile Tyr Glu Val Pro Ile Ile Thr Asp Ser Gly Asn
            515                 520                 525

Pro Pro Lys Ser Asn Ile Ser Ile Leu Arg Val Lys Val Cys Gln Cys
530                 535                 540

Asp Ser Asn Gly Asp Cys Thr Asp Val Asp Arg Ile Val Gly Ala Gly
545                 550                 555                 560

Leu Gly Thr Gly Ala Ile Ile Ala Ile Leu Leu Cys Ile Ile Ile Leu
                565                 570                 575

Leu Ile Leu Val Leu Met Phe Val Val Trp Met Lys Arg Arg Asp Lys
            580                 585                 590

Glu Arg Gln Ala Lys Gln Leu Leu Ile Asp Pro Glu Asp Asp Val Arg
            595                 600                 605

Asp Asn Ile Leu Lys Tyr Asp Glu Glu Gly Gly Gly Glu Glu Asp Gln
610                 615                 620

-continued

```
Asp Tyr Asp Leu Ser Gln Leu Gln Gln Pro Asp Thr Val Glu Pro Asp
625                 630                 635                 640

Ala Ile Lys Pro Val Gly Ile Arg Arg Met Asp Glu Arg Pro Ile His
            645                 650                 655

Ala Glu Pro Gln Tyr Pro Val Arg Ser Ala Ala Pro His Pro Gly Asp
        660                 665                 670

Ile Gly Asp Phe Ile Asn Glu Gly Leu Lys Ala Ala Asp Asn Asp Pro
    675                 680                 685

Thr Ala Pro Pro Tyr Asp Ser Leu Leu Val Phe Asp Tyr Glu Gly Ser
690                 695                 700

Gly Ser Thr Ala Gly Ser Leu Ser Ser Leu Asn Ser Ser Ser Ser Gly
705                 710                 715                 720

Gly Glu Gln Asp Tyr Asp Tyr Leu Asn Asp Trp Gly Pro Arg Phe Lys
                725                 730                 735

Lys Leu Ala Asp Met Tyr Gly Gly Gly Asp Asp
            740                 745

<210> SEQ ID NO 98
<211> LENGTH: 722
<212> TYPE: PRT
<213> ORGANISM: Homo sapiens
<220> FEATURE:
<221> NAME/KEY: misc_feature
<223> OTHER INFORMATION: P-CADHERIN

<400> SEQUENCE: 98

Asp Trp Val Val Ala Pro Ile Ser Val Pro Glu Asn Gly Lys Gly Pro
1               5                   10                  15

Phe Pro Gln Arg Leu Asn Gln Leu Lys Ser Asn Lys Asp Arg Asp Thr
            20                  25                  30

Lys Ile Phe Tyr Ser Ile Thr Gly Pro Gly Ala Asp Ser Pro Pro Glu
        35                  40                  45

Gly Val Phe Ala Val Glu Lys Glu Thr Gly Trp Leu Leu Leu Asn Lys
    50                  55                  60

Pro Leu Asp Arg Glu Glu Ile Ala Lys Tyr Glu Leu Phe Gly His Ala
65                  70                  75                  80

Val Ser Glu Asn Gly Ala Ser Val Glu Asp Pro Met Asn Ile Ser Ile
                85                  90                  95

Ile Val Thr Asp Gln Asn Asp His Lys Pro Lys Phe Thr Gln Asp Thr
            100                 105                 110

Phe Arg Gly Ser Val Leu Glu Gly Val Leu Pro Gly Thr Ser Val Met
        115                 120                 125

Gln Val Thr Ala Thr Asp Glu Asp Ala Ile Tyr Thr Tyr Asn Gly
    130                 135                 140

Val Val Ala Tyr Ser Ile His Ser Gln Glu Pro Lys Asp Pro His Asp
145                 150                 155                 160

Leu Met Phe Thr Ile His Arg Ser Thr Gly Thr Ile Ser Val Ile Ser
                165                 170                 175

Ser Gly Leu Asp Arg Glu Lys Val Pro Glu Tyr Thr Leu Thr Ile Gln
            180                 185                 190

Ala Thr Asp Met Asp Gly Asp Gly Ser Thr Thr Thr Ala Val Ala Val
        195                 200                 205

Val Glu Ile Leu Asp Ala Asn Asp Asn Ala Pro Met Phe Asp Pro Gln
    210                 215                 220

Lys Tyr Glu Ala His Val Pro Glu Asn Ala Val Gly His Glu Val Gln
225                 230                 235                 240
```

```
Arg Leu Thr Val Thr Asp Leu Asp Ala Pro Asn Ser Pro Ala Trp Arg
            245                 250                 255
Ala Thr Tyr Leu Ile Met Gly Gly Asp Gly Asp His Phe Thr Ile
            260                 265                 270
Thr Thr His Pro Glu Ser Asn Gln Gly Ile Leu Thr Thr Arg Lys Gly
            275                 280                 285
Leu Asp Phe Glu Ala Lys Asn Gln His Thr Leu Tyr Val Glu Val Thr
290                 295                 300
Asn Glu Ala Pro Phe Val Leu Lys Leu Pro Thr Ser Thr Ala Thr Ile
305                 310                 315                 320
Val Val His Val Glu Asp Val Asn Glu Ala Pro Val Phe Val Pro Pro
            325                 330                 335
Ser Lys Val Val Glu Val Gln Glu Gly Ile Pro Thr Gly Glu Pro Val
            340                 345                 350
Cys Val Tyr Thr Ala Glu Asp Pro Asp Lys Glu Asn Gln Lys Ile Ser
            355                 360                 365
Tyr Arg Ile Leu Arg Asp Pro Ala Gly Trp Leu Ala Met Asp Pro Asp
            370                 375                 380
Ser Gly Gln Val Thr Ala Val Gly Thr Leu Asp Arg Glu Asp Glu Gln
385                 390                 395                 400
Phe Val Arg Asn Asn Ile Tyr Glu Val Met Val Leu Ala Met Asp Asn
            405                 410                 415
Gly Ser Pro Pro Thr Thr Gly Thr Gly Thr Leu Leu Leu Thr Leu Ile
            420                 425                 430
Asp Val Asn Asp His Gly Pro Val Pro Glu Pro Arg Gln Ile Thr Ile
            435                 440                 445
Cys Asn Gln Ser Pro Val Arg His Val Leu Asn Ile Thr Asp Lys Asp
            450                 455                 460
Leu Ser Pro His Thr Ser Pro Phe Gln Ala Gln Leu Thr Asp Asp Ser
465                 470                 475                 480
Asp Ile Tyr Trp Thr Ala Glu Val Asn Glu Glu Gly Asp Thr Val Val
            485                 490                 495
Leu Ser Leu Lys Lys Phe Leu Lys Gln Asp Thr Tyr Asp Val His Leu
            500                 505                 510
Ser Leu Ser Asp His Gly Asn Lys Glu Gln Leu Thr Val Ile Arg Ala
            515                 520                 525
Thr Val Cys Asp Cys His Gly His Val Glu Thr Cys Pro Gly Pro Trp
            530                 535                 540
Lys Gly Gly Phe Ile Leu Pro Val Leu Gly Ala Val Leu Ala Leu Leu
545                 550                 555                 560
Phe Leu Leu Leu Val Leu Leu Leu Val Arg Lys Lys Arg Lys Ile
            565                 570                 575
Lys Glu Pro Leu Leu Leu Pro Glu Asp Asp Thr Arg Asp Asn Val Phe
            580                 585                 590
Tyr Tyr Gly Glu Glu Gly Gly Gly Glu Glu Asp Gln Asp Tyr Asp Ile
            595                 600                 605
Thr Gln Leu His Arg Gly Leu Glu Ala Arg Pro Glu Val Val Leu Arg
            610                 615                 620
Asn Asp Val Ala Pro Thr Ile Ile Pro Thr Pro Met Tyr Arg Pro Arg
625                 630                 635                 640
Pro Ala Asn Pro Asp Glu Ile Gly Asn Phe Ile Ile Glu Asn Leu Lys
            645                 650                 655
```

-continued

```
Ala Ala Asn Thr Asp Pro Thr Ala Pro Pro Tyr Asp Thr Leu Leu Val
        660             665             670

Phe Asp Tyr Glu Gly Ser Gly Ser Asp Ala Ala Ser Leu Ser Ser Leu
        675             680             685

Thr Ser Ser Ala Ser Asp Gln Asp Gln Asp Tyr Asp Tyr Leu Asn Glu
        690             695             700

Trp Gly Ser Arg Phe Lys Lys Leu Ala Asp Met Tyr Gly Gly Gly Glu
705             710             715             720

Asp Asp
```